US008626796B2

(12) United States Patent
McBride et al.

(10) Patent No.: US 8,626,796 B2
(45) Date of Patent: Jan. 7, 2014

(54) SYSTEM TO STORE AND ACCESS INFORMATION USED TO SCORE, GROUP AND PRESENT NUTRITIONAL VALUES OF FOOD PRODUCTS

(75) Inventors: James L. McBride, Windham, ME (US); Thomas A. Pike, Saco, ME (US)

(73) Assignee: Guiding Stars Licensing Company, Scarborough, ME (US)

( * ) Notice: Subject to any disclaimer, the term of this patent is extended or adjusted under 35 U.S.C. 154(b) by 1335 days.

(21) Appl. No.: 11/848,663

(22) Filed: Aug. 31, 2007

(65) Prior Publication Data

US 2008/0091705 A1 Apr. 17, 2008

Related U.S. Application Data

(63) Continuation-in-part of application No. 11/437,315, filed on May 19, 2006.

(51) Int. Cl.
*G06F 7/00* (2006.01)
*G06F 17/30* (2006.01)

(52) U.S. Cl.
USPC ........... 707/796; 707/756; 707/763; 707/805; 705/26.7; 705/27.2

(58) Field of Classification Search
USPC ............ 705/1, 14, 15, 26, 26.7, 27.2; 707/10, 707/100, 101, 102, 796, 756, 763, 805
See application file for complete search history.

(56) References Cited

U.S. PATENT DOCUMENTS

| | | | | |
|---|---|---|---|---|
| 5,412,560 | A | 5/1995 | Dennison | |
| 5,478,989 | A | 12/1995 | Shepley | |
| 5,726,899 | A | 3/1998 | Ferguson et al. | |
| 5,819,735 | A | 10/1998 | Mansfield et al. | |
| 5,841,115 | A * | 11/1998 | Shepley | 235/375 |
| 5,960,440 | A * | 9/1999 | Brenner et al. | 1/1 |
| 6,246,998 | B1 | 6/2001 | Matsumori | |
| 6,358,546 | B1 | 3/2002 | Bebiak et al. | |

(Continued)

FOREIGN PATENT DOCUMENTS

| | | |
|---|---|---|
| WO | 9803930 | 1/1998 |
| WO | WO 98/45766 | * 10/1998 |

OTHER PUBLICATIONS

NutriGenie, "Diet Quality Analysis", from Wayback Machine, Jan. 7, 2006, http://web.archive.org/web/20060107183254/http://nutrigenie.biz/ufdqa.html (3 pages).*

(Continued)

*Primary Examiner* — Shew-Fen Lin
(74) *Attorney, Agent, or Firm* — Verrill Dana, LLP; Chris A. Caseiro

(57) ABSTRACT

A database, system and related method for storing, retrieving, manipulating and presenting nutritional information about food items includes functions and data tables arranged to enable nutritional value scoring and rating. The database, system and method are arranged to enable users to input nutritional information deemed pertinent to assessing the nutritional value of food items. The tables of the database include entities representing food item designations, and arrangements of nutritional information. The nutritional information may be acquired from external sources or generated internally, including for prepared foods. The system is arranged to enable users to generate customized reports based on all product and/or company information of interest or any selectable portions of such information.

34 Claims, 26 Drawing Sheets

(56) References Cited

U.S. PATENT DOCUMENTS

| | | | | |
|---|---|---|---|---|
| 6,375,077 | B1 * | 4/2002 | Hankins | 235/462.45 |
| 6,663,564 | B2 | 12/2003 | Miller-Kovach et al. | |
| 6,796,507 | B2 | 9/2004 | Bean et al. | |
| 6,980,999 | B1 * | 12/2005 | Grana | 1/1 |
| 7,044,739 | B2 | 5/2006 | Matson | |
| 7,090,638 | B2 * | 8/2006 | Vidgen | 600/300 |
| 7,195,157 | B2 * | 3/2007 | Swartz et al. | 235/383 |
| 2002/0004749 | A1 | 1/2002 | Froseth et al. | |
| 2003/0054089 | A1 | 3/2003 | Prosise et al. | |
| 2003/0171944 | A1 * | 9/2003 | Fine et al. | 705/1 |
| 2004/0074675 | A1 | 4/2004 | Miller-Kovach et al. | |
| 2004/0078218 | A1 | 4/2004 | Badinelli | |
| 2005/0040230 | A1 * | 2/2005 | Swartz et al. | 235/383 |
| 2005/0042582 | A1 | 2/2005 | Graves | |
| 2005/0055860 | A1 | 3/2005 | Arrendale et al. | |
| 2005/0086080 | A1 | 4/2005 | Stump et al. | |
| 2005/0113649 | A1 | 5/2005 | Bergantino | |
| 2005/0256889 | A1 * | 11/2005 | McConnell | 707/100 |
| 2005/0260302 | A1 | 11/2005 | Prosise | |
| 2006/0018998 | A1 * | 1/2006 | Green et al. | 426/87 |
| 2006/0263750 | A1 | 11/2006 | Gordon | |
| 2006/0287810 | A1 | 12/2006 | Sadri et al. | |
| 2007/0038933 | A1 | 2/2007 | Luzzatto | |
| 2007/0059672 | A1 | 3/2007 | Shaw | |
| 2007/0191689 | A1 * | 8/2007 | Elitok | 600/300 |
| 2007/0226064 | A1 * | 9/2007 | Yu et al. | 705/20 |
| 2008/0086374 | A1 * | 4/2008 | Aitken et al. | 705/14 |
| 2008/0268103 | A1 | 10/2008 | Derks et al. | |

OTHER PUBLICATIONS

Aikman, S.N., et al., "Food attitudes, eating behavior and the information underlying food attitudes", Appetite, vol. 47, Issue 1, Jul. 2006, pp. 111-114, US.

Antonuk, Beth, et al., "The Effect of Single Serving Versus Entire Package Nutritional Information on Consumption Norms and Actual Consumption of a Snack Food", Journal of Nutritional Education and Behavior, vol. 38, Issue 6, Nov. 2006, pp. 365-370, US.

Blitstein, J.L., et al., "Use of Nutrition Facts Panels among Adults Who Make Household Food Purchasing Decisions", Journal of Nutrition Education and Behavior, vol. 38, Issue 6, Nov. 2006, pp. 360-364, US.

Bowman, S.A., "Food shoppers' nutrition attitudes and relationship to dietary and lifestyle practices", Nutrition Research, vol. 25, Issue 3, Mar. 2005, pp. 281-293, US.

Burton, S., et al., "Age, Product Nutrition, and Label Format Effects on Consumer Perceptions and Product Evaluations", Journal of Consumer Affairs, 30(1), pp. 68-69, US.

Chaftel, J.C., "Food and nutrition labeling in the European Union", Food Chemistry, vol. 93, Issue 3, Dec. 2005, pp. 531-550, US.

Charney, P.J. et al., "Reliability of Nutrition Diagnostic Labels When Used by Registered Dietitians at Three Levels of Practice", Journal of the American Dietetic Association, vol. 106, Issue 8, Suppl. 1, Aug. 2006, p. Al2, US.

Cunningham, J., et al., "Lessons learned from providing a free nutrition labeling tool for industry—the Australian experience", Journal of Food Composition and Analysis, vol. 17, No. 3-4, Jun.-Aug. 2004, pp. 565-574, US.

Edwards, J.U., et al., "Revision of the Food Guide Pyramid for Endurance Athletes Based on Carbohydrate Counting", Journal of the American Dietetic Association, vol. 99, Issue 9, Suppl. 1, Sep. 1999, p. A38, US.

Grunert, K.G., et al. "A review of European research on consumer response to nutrition information on food labels", Journal of Public Health, US.

Hawthorne, K.M., et al., "An Educational Program Enhances Food Understanding of Young Adolescents", Journal of the American Dietetic Association, vol. 106, Issue 6, Jun. 2006, pp. 913-916, US.

Marietta, A.B., et al., "Older Americans and the Nutrition Facts Food Labels", Journal of the American Dietetic Association, vol. 97, Issue 9, Suppl. 1, Sep. 1997, p. A113, US.

Moss, J., "Labeling of trans fatty acid content in food, regulations and limits—The FDA view", Atherosclerosis Supplements, vol. 7, Issue 2, May 2006, pp. 57-59, US.

Rothman, R.L., et al., "Patient Understanding of Food Labels: The Role of Literacy and Numeracy", American Journal of Preventive Medicine, vol. 31, Issue 5, Nov. 2006, pp. 391-398, US.

Satia, J.A. "Food nutrition label use is associated with demographic, behavioral, and psychosocial factors and dietary intake among African Americans in North Carolina", Journal of the American Dietetic Association, vol. 105, Issue 3, Mar. 2005, pp. 392-402, US.

Schoenbach, G., "An Attempt to Individualize Diabetes Medical Nutrition Therapy in Diabetes Classes", Journal of the American Dietetic Association, vol. 99, Issue 9, Suppl. 1, Sep. 199, p. A109, US.

Drewnowski, A., "Concept of a nutritious food: toward a nutrient density score", The American Journal of Clinical Nutrition, 2005, 721-732, vol. 82, American Society for Clinical Nutrition, US.

Zelman, K. et al., "Naturally Nutrient Rich . . . Putting More Power on Americans' Plates", Nutrition Today, Mar./Apr. 2005, 60-68, vol. 40, No. 2.

Scarborough, P. et al., "Developing nutrient profile models: a systematic approach", Public Health Nutrition, 2007, 330-336, vol. 10(4), The Authors, UK.

Rayner, M. et al., "Nutrient profiles: Applicability of currently proposed model for uses in relation to promotion of food to children aged 5-10 and adults", British Heart Foundation Health Promotion Research Group, Department of Public Health, University of Oxford, Jan. 2005, 14 pages, UK.

Darmon, N. et al., "A Nutrient Density Standard for Vegetables and Fruits: Nutrients per Calorie and Nutrients per Unit Cost", Journal of the American Dietetic Association, 2005, 1881-1887, American Dietetic Association, US.

Rayner, M. et al., "Nutrient profiles: Further refinement and testing of Model SSCg3d", British Heart Foundation Health Promotion Research Group, Department of Public Health, University of Oxford, Sep. 2005, 60 pages, UK.

Copy of screens "Wegmans Wellness Keys", (no date), website www.wegmans.comeatwelllivewell/healthyEating/wellnessKey.asp (2 pp).

Copy of screens "Have Food Allergies or Special Dietary Needs?", (May 6, 2005), www.wegmans.com/about/pressRoom/pressReleases/foodSensitivityEfforts.asp (2 pp).

Copy of screen "Key in on Wellness Keys", (Feb. 1, 2006), www.wegmans.com/meb/columns/021106a.asp (1 pp).

Copy of screen "Key in on Wellness Keys", (Apr. 9, 2006), www.wegmans.com/meb/content.asp?contentid=64 (1 pp).

Sugar and vending groups take offensive against obesity, Feb. 2005, Newsletter, Brief Article, Stagnito Communications, 2 pp.

Vending industry kicks off campaign targeting childhood obesity, Jan. 17, 2005, The Food Institute Report, No. 2, 2 pp.

Van Trijpa, Hans C.M., et al., "Consumer perceptions of nutrition health claims", Appetite, vol. 48, Issue 3, May 2007, pp. 305-324, US.

Scott, J., "Nutrition Profiling—Guiding Consumer Choice", BEUC/TACD Conference [online], Dec. 1, 2005. [retrieved on Oct. 5, 2007]. Retrieved from the Internet: <URL: http://www.tacd.org/events/ge2/j_scott.ppt>. 19 pages.

Seddon, Soy and Soy-based Foods.? National Heart Foundation of New Zealand's Nutrition Advisory Committee [online], Mar. 1999. [retrieved on Oct. 5, 2007]. Retrieved from the Internet: <URL: http://nhf.org.nz/files/National%20Dietitian/Soy%20and%20Soy-based%20Foods_March1999.pfd>. 11 pages.

International Search Report and Written Opinion for PCT/US07/69130, date of mailing: Nov. 15, 2007, 7 pages.

Katz, D.L., "The Food Supply for Dummies," First Published Oct. 6, 2003 in the Hartford Courant, Carolyn Lumsden, Op-Ed Editor, 4 pages.

Rayner, M., et al., "Nutrient profiles: Development of Final Mode, Final Report." British Heart Foundation Health Promotion Research Group, Department of Public Health, University of Oxford, Dec. 2005, 86 pages.

(56) References Cited

OTHER PUBLICATIONS

Western Australia Department of Health Submission to the Australian Communications and Media Authority Review of its Children's Television Standards, Nov. 2005, 13 pages.
Underwood, A., "Three-Star Snacks in Aisle Five", Newsweek, Nov. 12, 2007, 1 page.
Copy of screen "Key in on Wellness Keys", (Apr. 15, 2006), www.wegmans.com/meb/columns/041506ML.asp (1 pp).
Copy of screens "How to Understand and Use Nutrition Facts Label", (Jun. 2000-Nov. 2004), www.cfsan.fda.gov/~dms/foodlab.html (10 pp).

* cited by examiner

View Items

| Item List | Search |

Company: Hannaford
Product State: Items new to system

Item Listing : Items new to system

Items to be sent for nutritional info [ 971 ]

[Show List]

300

Download to Excel

| UPC ▲ | Description | Super Category | Category | Sub Category | Setup Date | Notes |
|---|---|---|---|---|---|---|
| 00000000000311 | Barry Cup | 024 Produce | 620 P-F-Cut Fruit | 20 In Store Produced | 05/22/2003 | ✍ |
| 00000000005140 | Bulk Gourmet Rolls (Fe) | 026 Bakery | 855 B–Rolls | 09 Bulk Rolls | 07/18/2007 | ▦ |
| 00008107822994 | Chicago Sea Slt Flat Brd | 025 Deli | 848 D–Miscellaneous | 25 Kehe Items | 05/26/2006 | ✍ |
| 00008346220793 | Di Optima Bar Pb Gran6+2 | 017 Edible Grocery | 034 Sp–Diet | 20 Meal Replacement | 07/11/2007 | ▦ |
| 00008346226730 | Di Optima Bar Oat Rais6+2 | 017 Edible Grocery | 034 Sp–Diet | 20 Meal Replacement | 07/11/2007 | ✍ |
| 00008346226731 | Di Optima Bar Ch Pnt 6+2 | 017 Edible Grocery | 034 Sp–Diet | 20 Meal Replacement | 07/17/2007 | ▦ |
| 00009800000669 | Tic Tac Citrus Twist 6Pk | 029 Gen Mdse | 003 Gm Candy & Gum | 16 Multipak Gum & Rolls | 07/17/2007 | ✍ |
| 00010700015311 | Jolly Rncr Frtas Enchda | 029 Gen Mdse | 003 Gm Candy & Gum | 60 All Peg Candy | 09/08/2004 | ▦ |
| 00011115170000 | Take Control Soft Tub | 050 Dairy | 300 Dr–Butter & Marg. | 70 Healthy Segment | 12/13/2001 | ▦ |
| 00011115178000 | Take Control Light Tub | 050 Dairy | 300 Dr–Butter & Marg. | 70 Healthy Segment | 12/13/2001 | ▦ |

<<Previous  Next>>

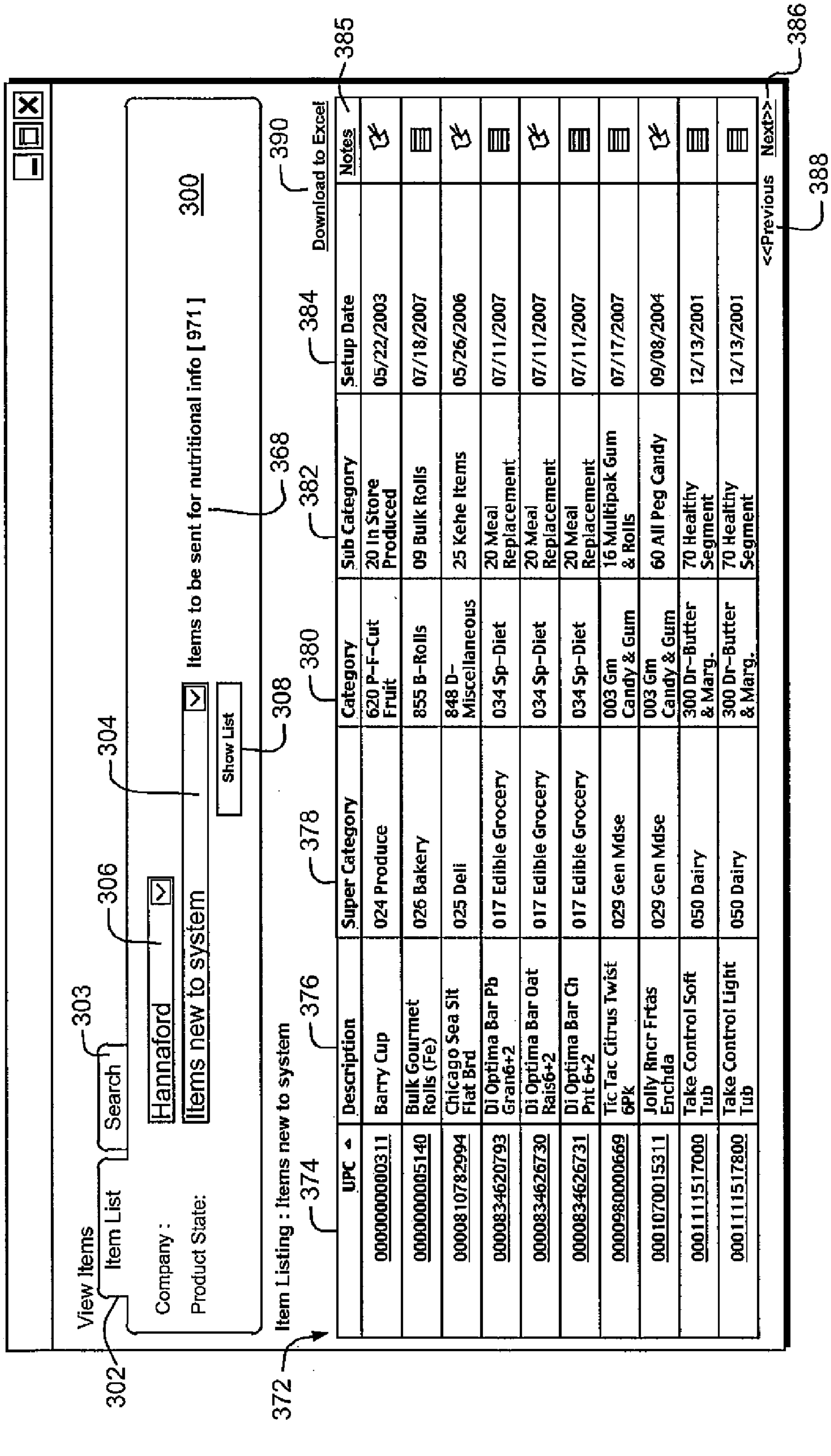

FIG. 6

Item Listing : Search

| UPC | Description | Super Category | Category | Sub Category | Product State | Notes |
|---|---|---|---|---|---|---|
| 00000000000101 | 8/5 Tote Rome Apples | 024 Produce | 600 P-F-Apples | 10 Apples Bagged | R | ✍ |
| 00000000000104 | Long Squash | 024 Produce | 670 P-V-Squash/pumkins | 20 Pumkins/squash Bulk | R | ✍ |
| 00000000000109 | Sliced Persian Melon | 024 Produce | 620 P-F-Cut Fruit | 20 In Store Produced | R | ✍ |
| 00000000000117 | Long Stem Collards | 024 Produce | 660 P-V-Cooking Greens | 10 Cooking Greens | R | ✍ |
| 00000000000120 | Squash Hubbard Cut | 024 Produce | 670 P-V-Squash/pumkins | 20 Pumkins/squash Bulk | R | ✍ |
| 00000000000123 | 8/5 Tote Empire | 024 Produce | 600 P-F-Apples | 10 Apples Bagged | R | ✍ |
| 00000000000130 | Plastic Lemon | 024 Produce | 610 P-F-Citrus Variety | 15 Squeeze Lemon & Lime | R | ▤ |
| 00000000000131 | Plastic Limes | 024 Produce | 610 P-F-Citrus Variety | 15 Squeeze Lemon & Lime | R | ▤ |
| 00000000000141 | Peeled Rutabagas (tump) | 024 Produce | 648 P-V-Precut Vegetable | 05 Precut Veg Bagged | R | ▤ |
| 00000000000199 | Sweet Onions | 024 Produce | 666 P-V-Onions | 10 Onions Bagged | R | ✍ |

<<Previous  Next>>

| Product Score and Report | Star Comparison Report | Item Star Listing Report |

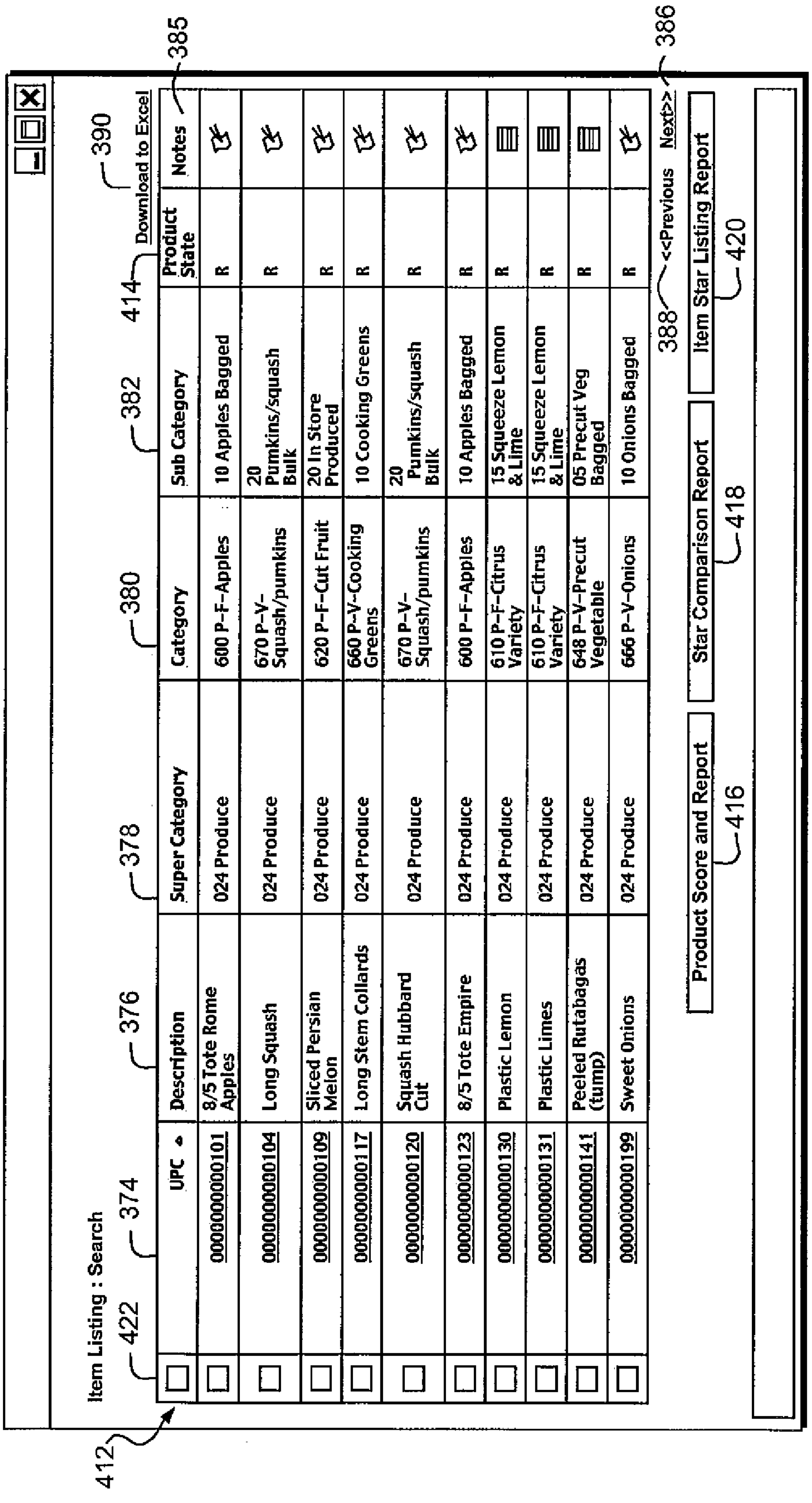

FIG. 7

Item Information

*The recalculated ratings will be saved to the database by batch process by end of week

| | | | |
|---|---|---|---|
| Company : | Hannaford | * UPC : | 001115200506 |
| Description : | Dynast Wasabi Mayona | Super Category : | Edible Grocery |
| Category : | Sp-Asian | Sub Category : | Sp-Asian |
| Post Date : | 04/11/2006 | | |
| Star Rating : | (Points -1) | Recalculated Rating : | (Points -1) |
| Tracking Notes : | | Product Rated with Flag : | G |

Product size (net wt) : 354.0 [ml] — 428

Serving Size : 1 [TBSP]

Brand : Dynasty — 430

Product Description : Wasabi Mayonnaise — 434

Ingredients : Pure Soybean Oil, Water, Whole Eggs, Apple Cider Vinegar, Horseradish, Egg Yolks, Salt, Mustard Flour, Lemon Juice Concentrate, Mustard Oil, Fd&c Yellow No. 5, Fd&c Blue No. 1, Natural Flavor. — 438

Product State: R — 424

Serving Per Container: 22 — 426, 428

Manufacturer : Jfc International, Inc. — 432

Warnings : Wasabi Mayonnaise — 436

440 — Save    Reset — 442

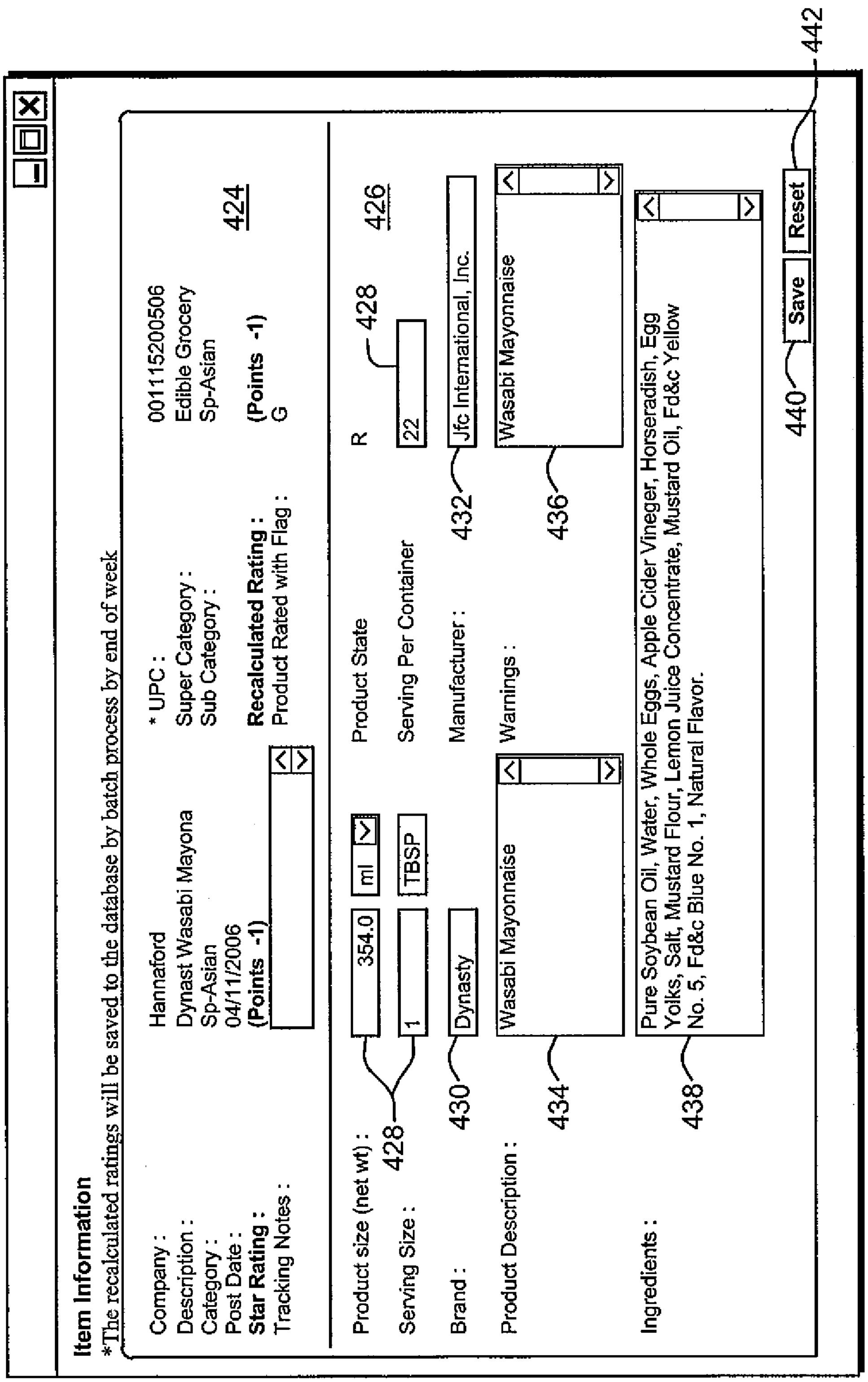

FIG. 8

| Nutrient Information ─444 ┌─446 ┌─448 ┌─450 | | | |
|---|---|---|---|
| Base Nutrients │ Vitamins │ Minerals │ Other Nutrients | | Product Score Card ─458 | Product Score Card - New ─476  Product Score Card - Old ─474 |

| Nutrient Name | Quantity ─454 ─456 | Unit of Measure ─460 | % Daily Value ─462 |
|---|---|---|---|
| Calories | 40.0 | kcal | 0 |
| Saturated Fat | 0.0 | g | 0 |
| Monounsaturated Fat | 0.0 | g | 0 |
| Cholesterol | 0.0 | mg | 0 |
| Sodium | 0.0 | mg | 0 |
| Potassium | 350.0 | mg | 10 ─464 |
| Dietary Fiber | 2.0 | g | 8 |
| Sugars | 2.0 | g | 0 |

452

─466 Save   ─468 Reset
─470 Recalculate   ─472 Do Not Rate

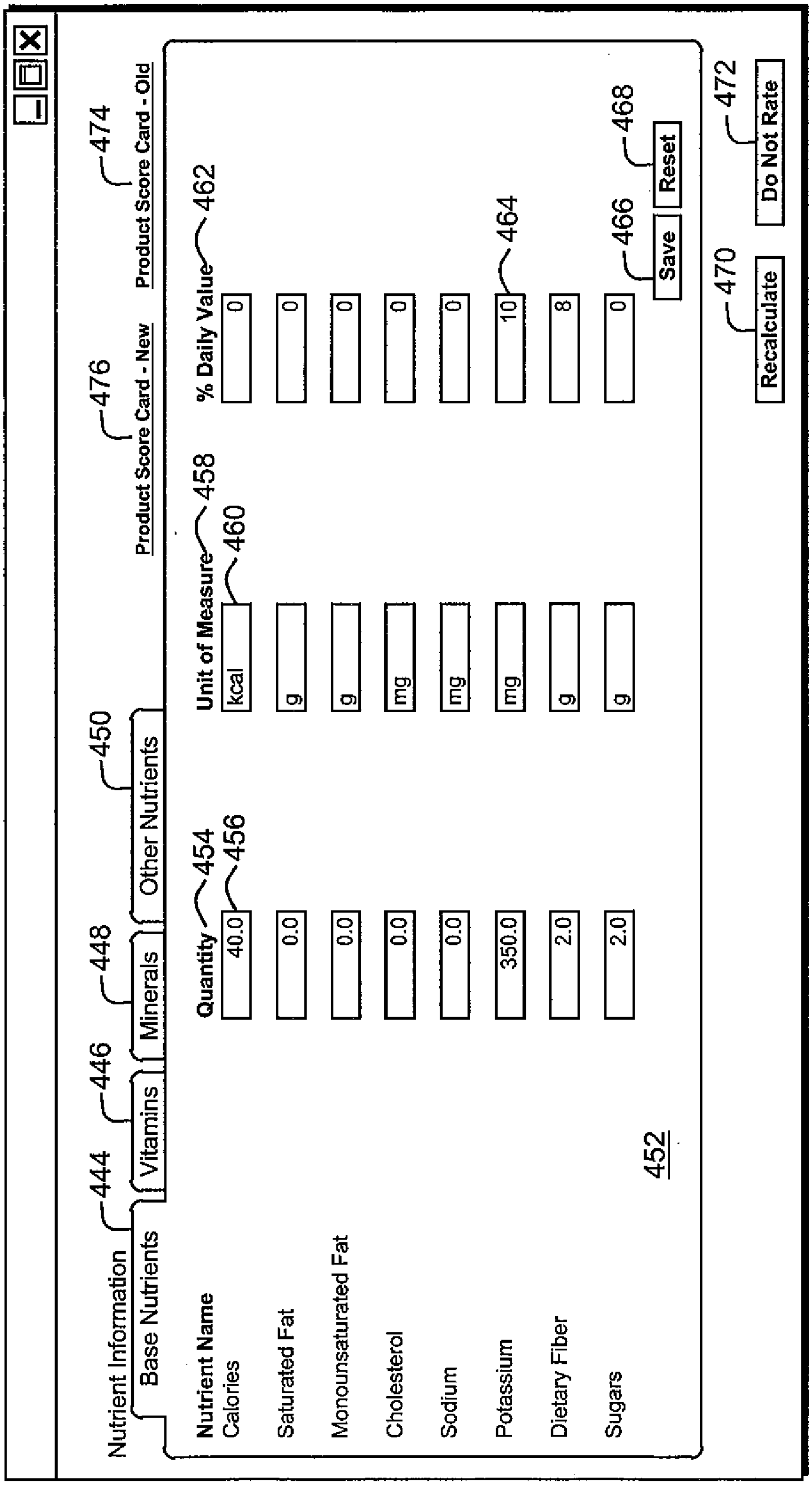

FIG. 9

| Nutrient Information | | | |
|---|---|---|---|
| Base Nutrients | Vitamins | Minerals | Other Nutrients |

Product Score Card - New ~476

Product Score Card - Old ~474

478

Nutrient Name    % Daily Value ~480 / ~482

| Vitamin A | 8 |
| Vitamin C | 20 |
| Vitamin D | 0 |
| Vitamin E | 0 |
| Folate | 4 |
| Pantothenic Acid | 4 |
| Vitamin B12 | 0 |
| Vitamin B6 | 8 |

446

Save ~466    Reset ~468

Recalculate ~470    Do Not Rate ~472

Nutrient Information

Base Nutrients | Vitamins | Minerals — 448 | Other Nutrients

Product Score Card — New — 476
Product Score Card — Old — 474

| Nutrient Name | % Daily Value — 486 / 488 |
|---|---|
| Potassium | 10 |
| Calcium | 4 |
| Iron | 4 |
| Copper | 4 |
| Magnesium | 8 |
| Manganese | 8 |
| Molybdenum | 6 |
| Phosphorus | 4 |
| Selenium | 0 |
| Zinc | 0 |

484

Save — 466
Reset — 468
Recalculate — 470
Do Not Rate — 472

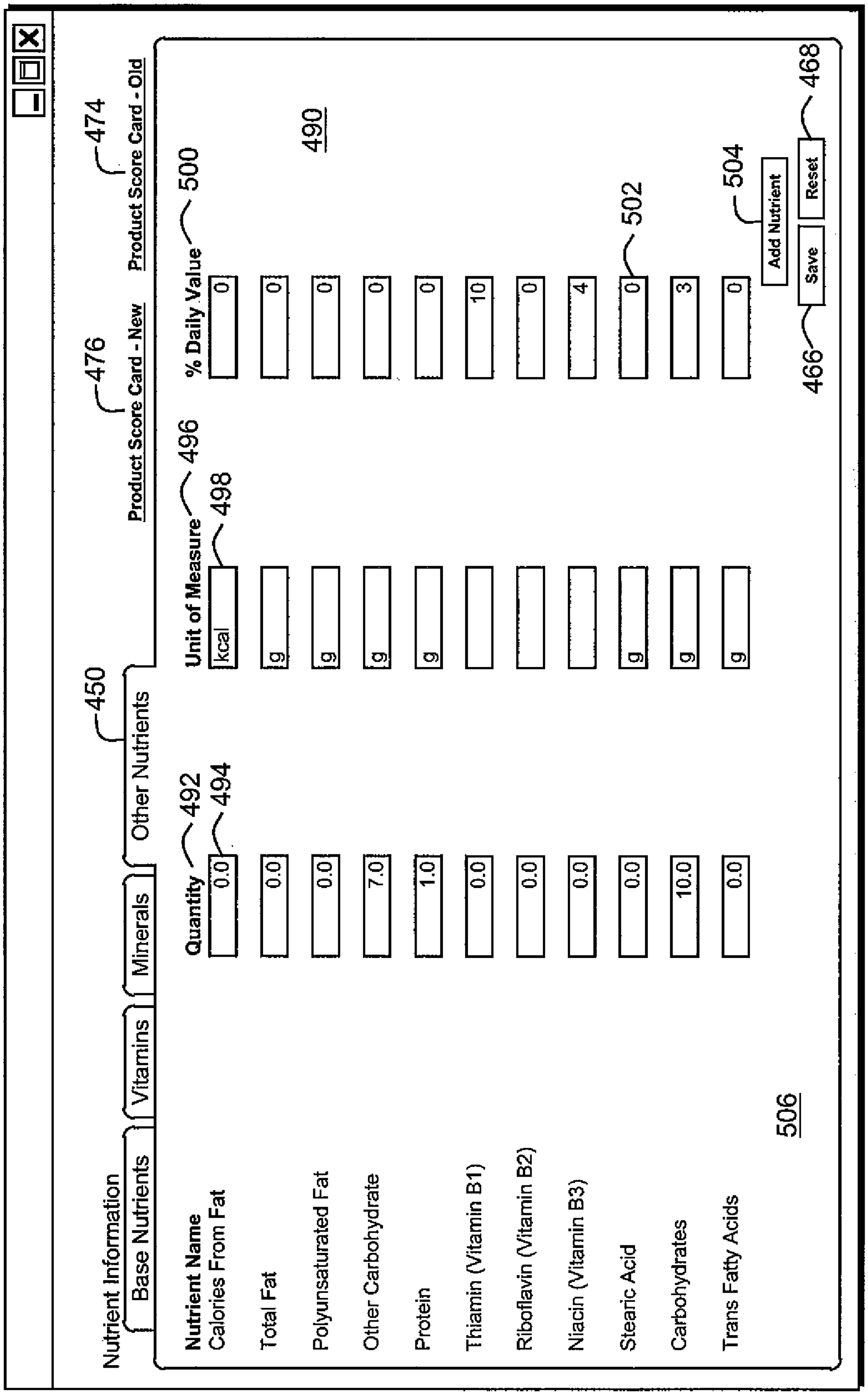

FIG. 12

Nutrient Information
Base Nutrients | Vitamins | Minerals | Other Nutrients ~450

Product Score Card — New ~476    Product Score Card — Old ~474

| Nutrient Name | Quantity ~492/494 | Unit of Measure ~496/498 | % Daily Value ~500 |
|---|---|---|---|
| Calories From Fat | 0.0 | kcal | 0 |
| Total Fat | 0.0 | g | 0 |
| Polyunsaturated Fat | 0.0 | g | 0 |
| Other Carbohydrate | 7.0 | g | 0 |
| Protein | 1.0 | g | 0 |
| Thiamin (Vitamin B1) | 0.0 | | 10 |
| Riboflavin (Vitamin B2) | 0.0 | | 4 |
| Niacin (Vitamin B3) | 0.0 | g | 0 ~502 |
| Stearic Acid | 0.0 | g | 3 |
| Carbohydrates | 10.0 | g | 0 |
| Trans Fatty Acids | 0.0 | | |

~506    ~490

Add Nutrient ~504
Save   Reset ~468
~466

Old Product Score Card Report (In Calories)
Item Information

| | | | |
|---|---|---|---|
| Company : | Hannaford | Description : | Chunky Beef W/wht&wild |
| UPC : | 005100013271 | Super Category : | Edible Grocery |
| Category : | Ge-Canned Soup | Sub Category : | Ready To Serve Soups |
| Star Rating : | No Stars (Points -11) | | |
| Tracking Notes : | Audited 9-25-07. Changed 09/26/07 | Post Date : | 09/26/2007 |
| Product Rated With Flag : | G | Audit Date : | |
| Product size(net wt) : Serving Size | 533.10 g | Serving Per Container | |
| Brand : | Campbell's | Manufacturer : | Campbell Soup Company |
| Product Description : | Campbell's Chunky Beef With White & Wild Rice Soup | Warnings : | Contains : wheat, Soy |
| Ingredients : | Water, Seasoned Cooked Beef (Contains Up To 10% Solution of Water, Salt, Sodium Phosphate), Cooked Rice, Carrots, Tomato Purse, Tomato Paste), Potatoes, Green Beans, Beef Flavor Base (Roasted Beef) And Natural Beef Juices, Hydrolyzed Corn Gluten, Soy and Wheat Protein, Grill Flavor (Flavor From Vegetable Pol, Modified Food Starch, Corn Syrup Solids), Salt, Toasted Wheat Germ, Maltodextrin, Flavoring, Corn Oil, Potato Flour, Caramel Color, Sugar), Corn, Celery, Wild Rice, Contains Less Than 1% Of: Modified Wheat Starch, Dehydrated Onions, Sugar, Monosodium Glutamate, Onion Powder, Roasted Vegetables (Carrots, Onions, Celery), Salt, Dehydrated Parsley, Potato Flour, Autolyzed Yeast Extract, Spice Extract, Flavoring, Caramel Color, Disodium Inosinate And Disodium Guanylate. | | |

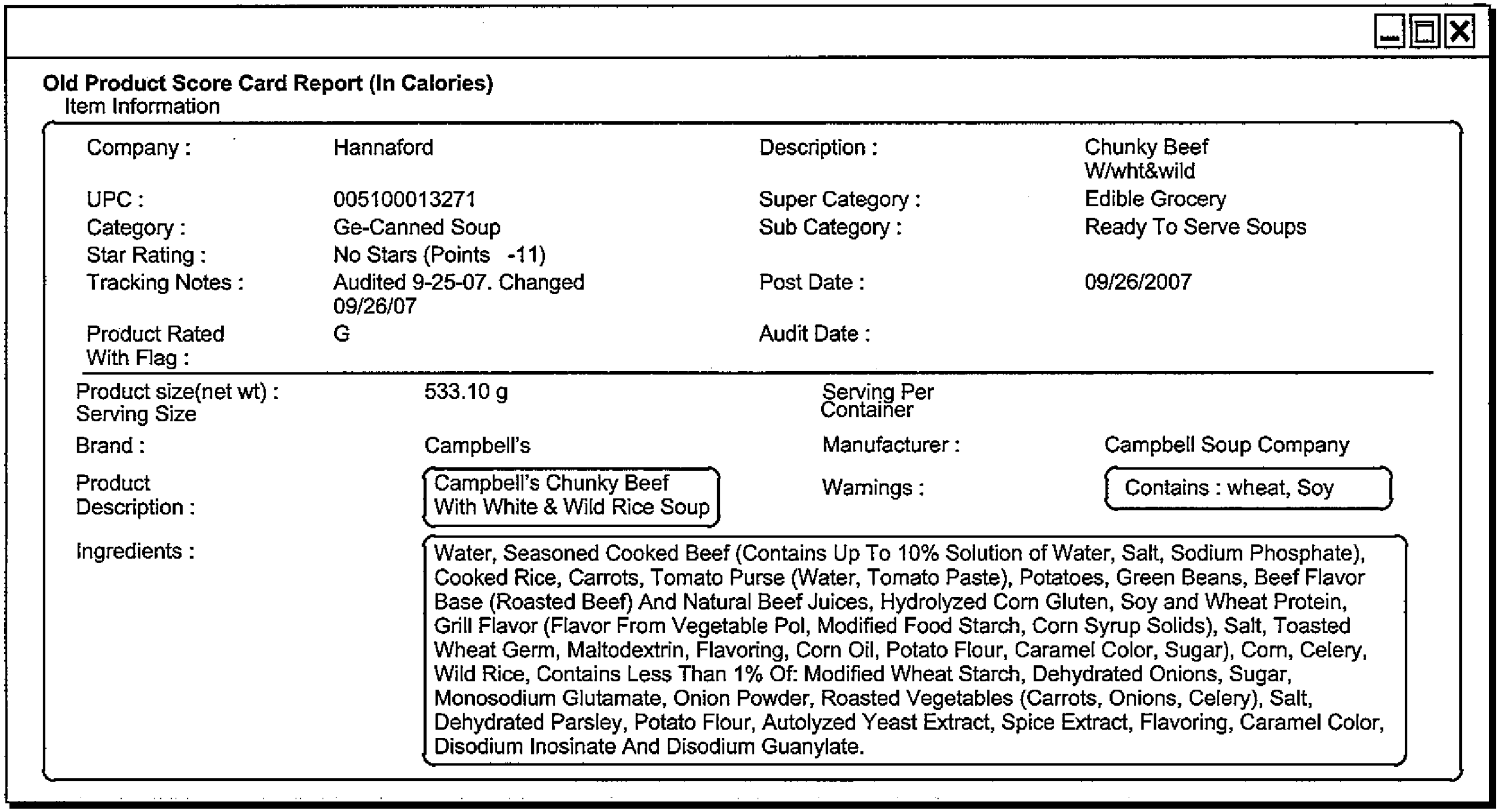

FIG. 13A

Element Point Mapping

508

| Element Name 512 | Element Quantity (Standard Serving Size) 514 | Element Total Points 516 |
|---|---|---|
| Trans Fatty Acid | 0g | -1 |
| Saturated Fat | 1.33g | -1 |
| Cholesterol | 6.67mg | 0 |
| Added Sugar | 13.33%kcal | -2 |
| Dietary Fiber | 1.33g | 1 |
| Sodium | 640mg | -10 |
| Nutrient Density | 1 nutrients (10%DV) | 2 |
| Whole Grain | 0y | 0 |
| Total | 0 | -11 |

518 520 522

Nutrition Facts Panel

510

| Servings Per Container : | Mfg. Serving Size - 160.0 cal | | | Standard Serving Size - 100 cal | | |
|---|---|---|---|---|---|---|
| Nutrient Name | Quantity | Unit of Measure | % | Quantity | Unit of Measure | (%) |
| Cholesterol | 10 | mg | 3 | 6.2 | mg | 2 |
| Dietary Fiber | 2 | g | 8 | 1.2 | g | 5 |
| Saturated Fat | 2 | g | 8 | 1.2 | g | 5 |
| Sodium | 960 | mg | 40 | 600 | mg | 25 |
| Sugars | 5 | g | 0 | 3.1 | g | 0 |
| Trans Fat | 0 | g | 0 | 0 | g | 0 |
| Protein | 0 | NA | 0 | 0 | NA | 0 |
| Vitamin A | NA | | 70 | NA | | 44 |
| Calcium | NA | | 2 | NA | | 1 |
| Iron | NA | | 6 | NA | | 4 |

FIG. 13B

Revised Product Score Card Report (In Calories)
Item Information

| | | | |
|---|---|---|---|
| Company : | Hannaford | Description : | Chunky Beef W/whit&wild |
| UPC : | 0051000013271 | Super Category : | Edible Grocery |
| Category : | Ge-Canned Soup | Sub Category : | Ready To Serve Soups |
| Star Rating : | No Stars (Points -11) | Recalculated Rating : | No Stars (Points -8) |
| Tracking Notes : | Audited 9-25-07. Changed 09/26/07 | Post Date : | 09/26/2007 |
| Product Rated With Flag : | G | Audit Date : | |
| Product size(net wt) : Serving Size | 533.10 g 240 ml | Serving Per Container | 2 |
| Brand : | Campbell's | Manufacturer : | Campbell Soup Company |
| Product Description : | Campbell's Chunky Beef With White & Wild Rice Soup | Warnings : | Contains : wheat, Soy |
| Ingredients : | Water, Seasoned Cooked Beef (Contains Up To 10% Solution of Water, Salt, Sodium Phosphate), Cooked Rice, Carrots, Tomato Purse (Water, Tomato Paste), Potatoes, Green Beans, Beef Flavor Base (Roasted Beef) And Natural Beef Juices, Hydrolyzed Corn Gluten, Soy and Wheat Protein, Grill Flavor (Flavor From Vegetable Pol, Modified Food Starch, Corn Syrup Solids), Salt, Toasted Wheat Germ, Maltodextrin, Flavoring, Corn Oil, Potato Flour, Caramel Color, Sugar), Corn, Celery, Wild Rice, Contains Less Than 1% Of: Modified Wheat Starch, Dehydrated Onions, Sugar, Monosodium Glutamate, Onion Powder, Roasted Vegetables (Carrots, Onions, Celery), Salt, Dehydrated Parsley, Potato Flour, Autolyzed Yeast Extract, Spice Extract, Flavoring, Caramel Color, Disodium Inosinate And Disodium Guanylate. | | |

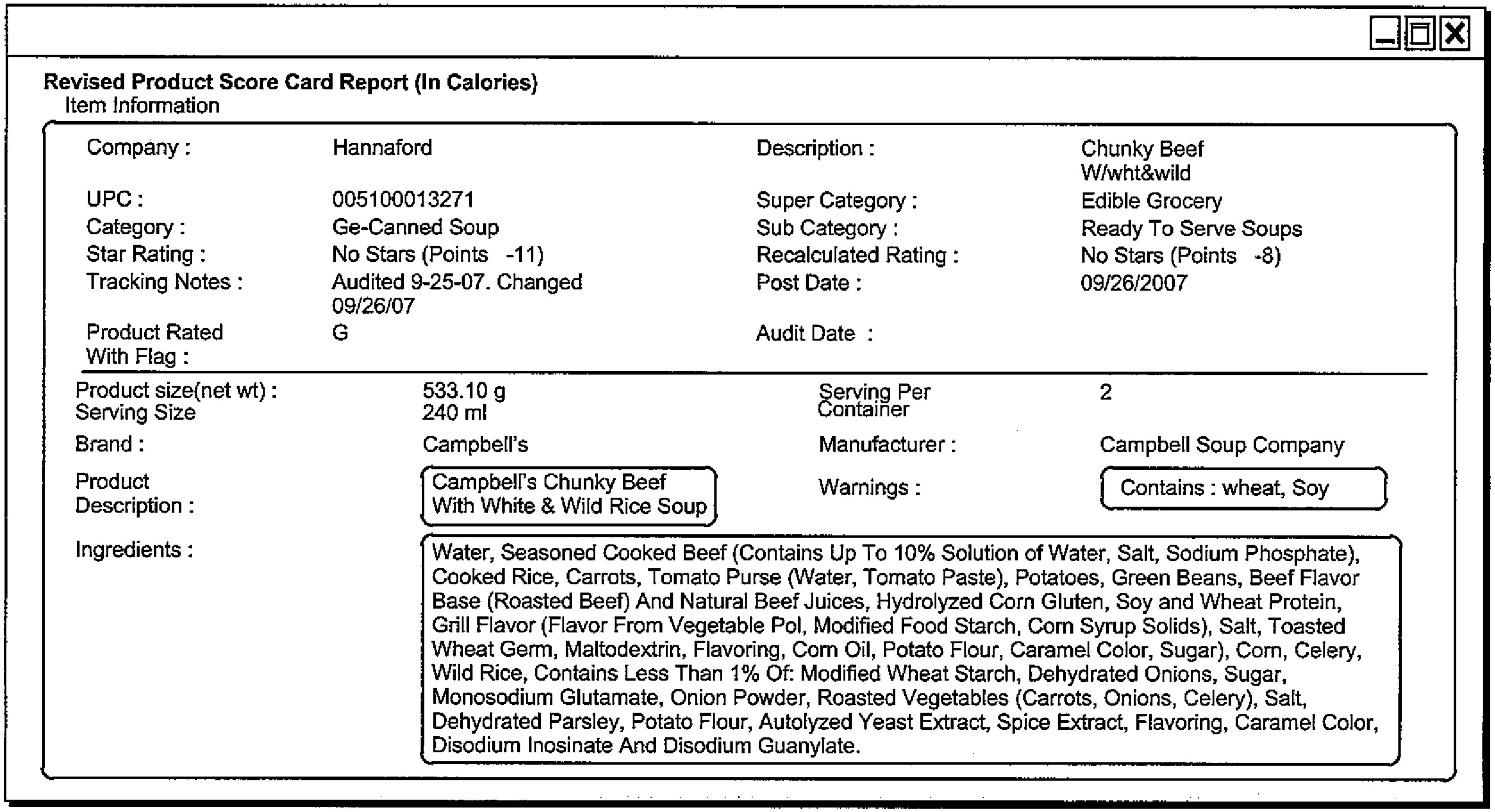

FIG. 14A

Element Point Mapping

508

| Element Name 512 | Element Quantity (Standard Serving Size) 514 | Element Total Points 516 |
|---|---|---|
| Trans Fatty Acid | 0g | 0 |
| Saturated Fat | 0.63g | 0 |
| Cholesterol | 6.25mg | 0 |
| Added Sugar | 12.5%kcal | -2 |
| Dietary Fiber | 1.88g | 1 |
| Sodium | 618.75mg | -10 |
| Nutrient Density | 1 nutrients (10%DV) | 2 |
| Whole Grain | 0y | 1 |
| Total | 0 | -8 |

518

Nutrition Facts Panel 510 520 522

| Servings Per Container : 2 | Mfg. Serving Size - 160.0 cal | | | Standard Serving Size - 100 cal | | |
|---|---|---|---|---|---|---|
| Nutrient Name | Quantity | Unit of Measure | % | Quantity | Unit of Measure | (%) |
| Saturated Fat | 1 | g | 5 | 0.6 | g | 3 |
| Monounsaturated Fat | 0 | | 0 | 0 | | 0 |
| Cholesterol | 10 | mg | 3 | 6.2 | mg | 2 |
| Sodium | 990 | mg | 41 | 618.8 | mg | 26 |
| Potassium | 0 | | 0 | 0 | | 0 |
| Dietary Fiber | 3 | g | 12 | 1.9 | g | 8 |
| Sugars | 5 | g | 0 | 3.1 | g | 0 |
| Trans Fat | 0 | g | 0 | 0 | g | 0 |
| Protein | 8 | g | 0 | 5 | g | 0 |
| Vitamin A | NA | | 50 | NA | | 31 |
| Calcium | NA | | 2 | NA | | 1 |
| Iron | NA | | 6 | NA | | 4 |

FIG. 14B

Figure 15:
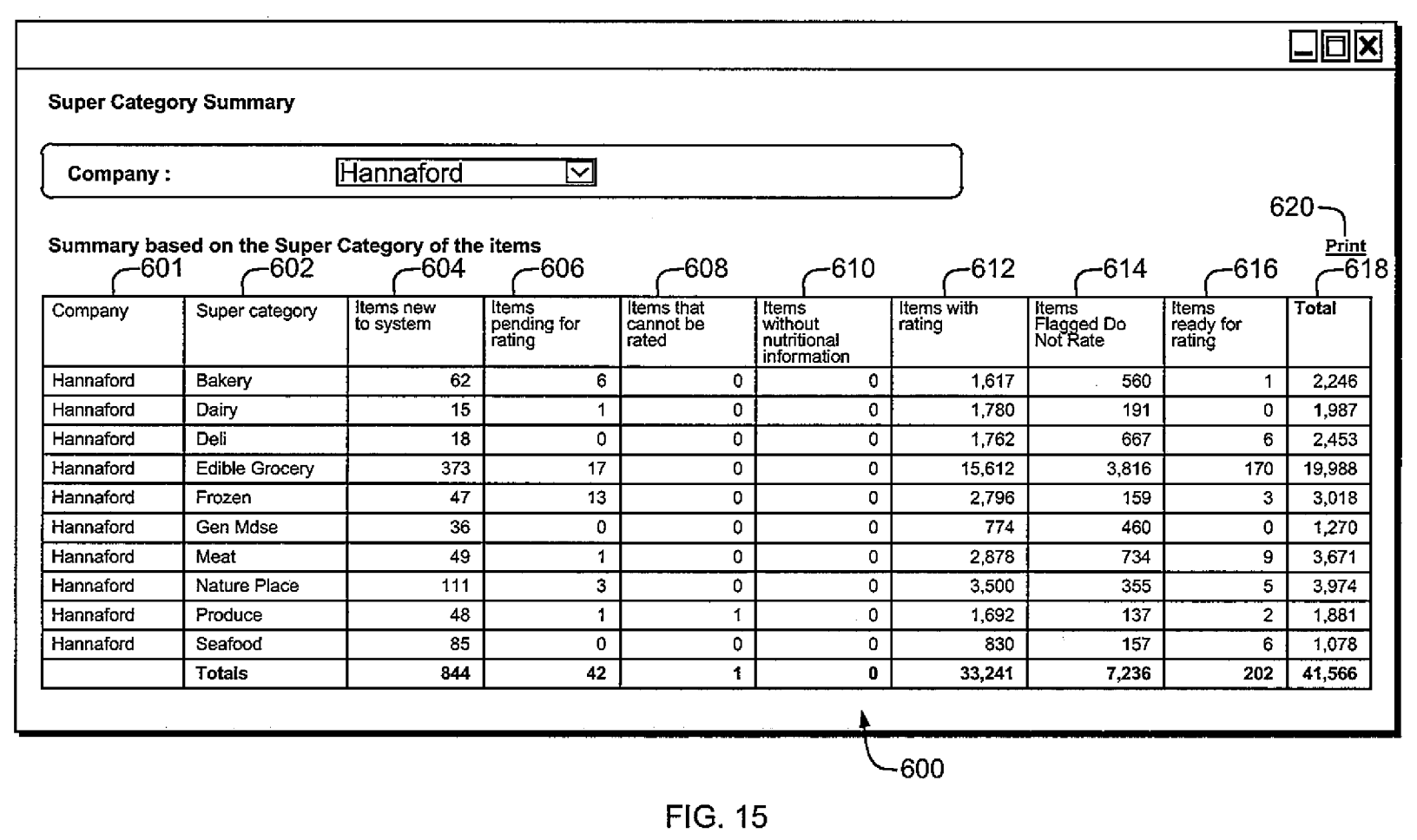

Super Category Summary

Company : Hannaford

620 Print

Summary based on the Super Category of the items

| Company (601) | Super category (602) | Items new to system (604) | Items pending for rating (606) | Items that cannot be rated (608) | Items without nutritional information (610) | Items with rating (612) | Items Flagged Do Not Rate (614) | Items ready for rating (616) | Total (618) |
|---|---|---|---|---|---|---|---|---|---|
| Hannaford | Bakery | 62 | 6 | 0 | 0 | 1,617 | 560 | 1 | 2,246 |
| Hannaford | Dairy | 15 | 1 | 0 | 0 | 1,780 | 191 | 0 | 1,987 |
| Hannaford | Deli | 18 | 0 | 0 | 0 | 1,762 | 667 | 6 | 2,453 |
| Hannaford | Edible Grocery | 373 | 17 | 0 | 0 | 15,612 | 3,816 | 170 | 19,988 |
| Hannaford | Frozen | 47 | 13 | 0 | 0 | 2,796 | 159 | 3 | 3,018 |
| Hannaford | Gen Mdse | 36 | 0 | 0 | 0 | 774 | 460 | 0 | 1,270 |
| Hannaford | Meat | 49 | 1 | 0 | 0 | 2,878 | 734 | 9 | 3,671 |
| Hannaford | Nature Place | 111 | 3 | 0 | 0 | 3,500 | 355 | 5 | 3,974 |
| Hannaford | Produce | 48 | 1 | 1 | 0 | 1,692 | 137 | 2 | 1,881 |
| Hannaford | Seafood | 85 | 0 | 0 | 0 | 830 | 157 | 6 | 1,078 |
| | **Totals** | **844** | **42** | **1** | **0** | **33,241** | **7,236** | **202** | **41,566** |

Existing:Cholesterol

| Point | Range | Value | Unit of Measure |
|-------|-------|-------|-----------------|
| 0 | <= | 15.0 | mg |
| -1 | <= | 30.0 | mg |
| -2 | <= | 45.0 | mg |
| -3 | > | 45.0 | mg |
| 0 | = | 0.0 | NA |

Nutrient Keywords : | Cholesterol | ◁ ▷ |

Ingredient Keywords : | | ◁ ▷ |

_674_

Modified:Cholesterol

| Point | Range | Value | Unit of Measure |
|-------|-------|-------|-----------------|
| 0 | <= | 15.0 | mg |
| -1 | <= | 30.0 | mg |
| -2 | <= | 45.0 | mg |
| -3 | > | 45.0 | mg |
| 0 | = | 0.0 | NA |

Nutrient Keywords : | Cholesterol | ◁ ▷ |

Ingredient Keywords : | | ◁ ▷ |

_676_

"Please review the rules before saving"
Complete recalculation of products available under GuidingStars application will take place on Save 680 — Save    Cancel — 678

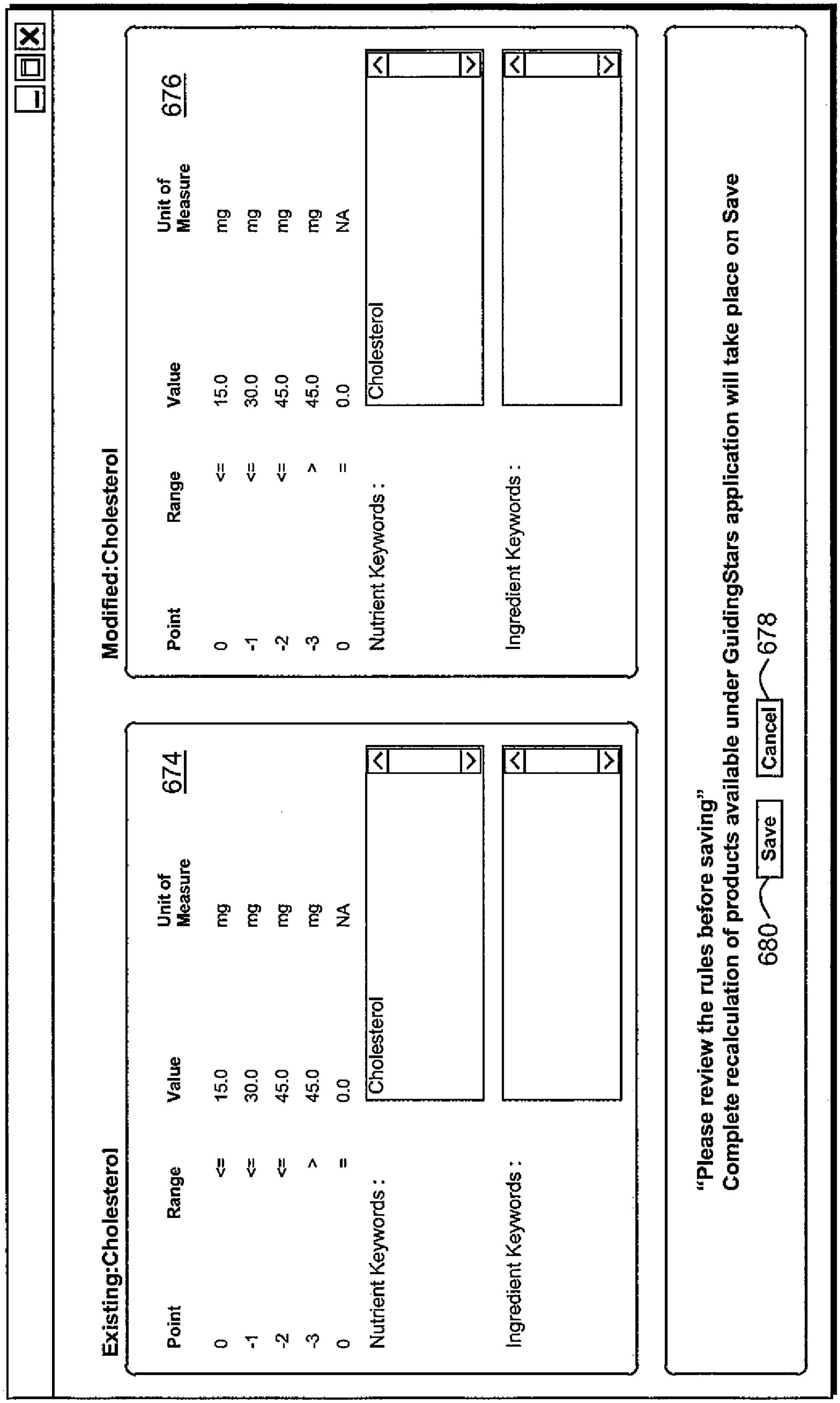

FIG. 17

GUIDING STARS

| View Items | View Super Category | Element Rule Mapping | Star Point Mapping | Copy Nutritional Value |
|---|---|---|---|---|

Generate Reports — 355

- ☐ Star wise Super Category Report — 716
- ☐ Star wise Category Report — 718

Company : [Hannaford ▽] — 720
Company : [Hannaford ▽] — 722

714

[Submit]

USER :
Home | Help
Reports

SYSTEM TO STORE AND ACCESS INFORMATION USED TO SCORE, GROUP AND PRESENT NUTRITIONAL VALUES OF FOOD PRODUCTS

CROSS REFERENCE TO RELATED APPLICATION

The present application is a continuation-in-part of, and claims priority benefit in, U.S. nonprovisional application Ser. No. 11/437,315, filed May 19, 2006, entitled "METHOD AND SYSTEM FOR ASSESSING, SCORING, GROUPING AND PRESENTING NUTRITIONAL VALUE INFORMATION OF FOOD PRODUCTS" assigned to a common assignee. The entire content of that priority application is incorporated herein by reference.

BACKGROUND OF THE INVENTION

1. Field of the Invention

The present invention relates to organizing and retaining information associated with food products. In particular, the present invention relates to characterizing the nutritional value of foods in a standardized way, establishing food nutritional value designations, and presenting that information in a readily observable manner.

2. Description of the Prior Art

Hannaford Bros. Co. of Scarborough, Me., an affiliate of the assignee of the present invention, has developed a system and method to assess and score food products based on nutritional value, which system and method are identified by the Guiding Stars$^{SM}$ mark. The system and method are described in detail in the priority application identified herein. The system requires a database of food product nutritional information used in an algorithm to determine a food nutrition score. Any commercially available databases suitable for use in the original development of the algorithm, comprised an insufficient number of products. Further, the required nutritional information had to be extracted manually and arranged in a form suitable for use with the algorithm. As a result of the inadequacy of the available information, the inventors recognized that a new database would be required in order to gather the type of information needed in the form needed for a comprehensive set of food items, including prepared foods.

While the initial development of the system involved the use of a sufficient number of sets of food nutritional data, it was soon discovered that the existing information available at the time did not: 1) include all food products offered to consumers; 2) include as much nutritional information as desired to fully implement the scoring algorithm; and 3) come in a form suitable for efficient processing through the scoring system. Therefore, what is needed is a food nutritional information gathering and storage system suitable to enable a comprehensive food nutritional value scoring system. Further, what is needed is such a gathering and storage system flexible enough to adapt to changes in nutritional information for any food product, including packaged and prepared foods. Yet further, what is needed is a food nutritional information gathering and storage system arranged to enable easy access to specific information of interest for any application of interest.

SUMMARY OF THE INVENTION

It is an object of the present invention to provide a food nutritional information gathering and storage system suitable to enable a comprehensive food nutritional value scoring system. It is also an object of the present invention to provide such a gathering and storage system flexible enough to adapt to changes in nutritional information for any food product, including packaged and prepared foods. Further, it is an object of the present invention to provide a food nutritional information gathering and storage system arranged to enable easy access to specific information of interest for any application of interest.

These and other objects of the present invention are achieved through a database configured to organize food information in a format that allows for information updates, information processing and information output controllable by a user. The database is a relational database comprising an expandable set of tables with relationships designed to carry out the goal of scoring food nutritional value for any food product for which nutritional information is available. The tables contain food information including, but not limited to, food nutritional information. The database is arranged to allow for changes in food information, as well as additions and deletions of food items. The database includes access authorization restrictions to ensure that only designated personnel can input or change information. The access to the information contained in the database may be more widespread than access to the information change function.

The present invention further includes computer programming to implement steps associated with accessing the information of the database and producing outputs associated with the performance of the nutritional value algorithm or other functions of interest involving use of the nutritional information of the database. Principal steps include, but are not limited to: 1) establishing a unique product identifier; 2) determining whether it has one or more ingredients and/or is a prepared food; 3) determining whether the product is already stored in the database; 4) determining whether the product has enough calories to be included in the database for nutritional scoring purposes; 5) entering nutritional information for the product either directly from a label or through an ingredient nutritional value determination; 6) running the entered nutritional information through the algorithm to establish a nutritional value; 7) determining for an existing product with changed nutritional information whether the value rating for the product should be changed; 8) auditing the system for new and changed value rating designations; and 9) activating a changed tag process for new and changed products with new value ratings.

The invention includes a database comprising one or more food product information tables including entities for: identifying one or more food products, each by a unique identifier, listing ingredients of each food product, and listing nutritional information of each food product, and one or more nutritional element mapping tables, each including fields for identifying nutritional value element mapping based on food product nutritional information. The database also includes one or more star rating mapping tables for designating a rating algorithm type for one or more of the one or more food products and a product label table that includes entities for food product super category and category. Additional tables of the database include a recipe table, a nutrition master table, an elements point table, a sub elements table, and an exceptions table, but is not limited thereto. The one or more food product information tables include entities for food base nutrients, vitamins and minerals. The database is arranged to enable a user to selectably display nutritional information and rating information for one or more of the one or more food products based on nutritional rating, company name or other selectable filtering options. The database is also arranged to group the one or more food items based on product state selected from the group consisting of items new to system, items pending for rating, items rated, items flagged do not rate and items ready for rating. The database is arranged to enable a user to modify food product ingredient or nutritional information and recalculate the star rating and to set up a dummy food product type, calculate a star rating for the dummy food product, modify nutritional information for the dummy food product, and recalculate the star rating.

The invention further includes a memory for storing data for access by an application program being executed on a computer processing system, comprising a data structure stored in the memory, the data structure including information resident in a database used by the application program, the database including one or more food product information tables including entities for: identifying one or more food products, each by a unique identifier, listing ingredients of each food product, and listing nutritional information of each food product, and one or more nutritional value mapping tables, each including fields for identifying nutritional value element mapping based on food product nutritional information. The memory includes the features of the database described herein.

The invention also contemplates the use of one or more computer-readable media comprising computer-executable instructions that, when executed, direct a computing system to maintain a database comprising: one or more food product information tables including entities for: identifying one or more food products, each by a unique identifier, listing ingredients of the one or more food products, and listing nutritional information of each food product, and a nutritional value mapping function including fields for identifying nutritional value element mapping based on food product nutritional information. The media further include a star rating function for designating a rating algorithm type for each food product and computer-executable instructions to enable a user to selectably display nutritional information and rating information for one or more of the one or more food products based on nutritional rating. Other computer-executable instructions of the media enable the user to selectably display nutritional information and rating information for one or more of the one or more food products based on company name, group the one or more food items based on product state selected from the group consisting of items new to system, items pending for rating, items rated, items flagged do not rate and items ready for rating, calculate a star rating based on product nutritional information, nutritional value mapping and rating algorithm type, modify food product ingredient or nutritional information and recalculate the star rating, or to set up a dummy food product type, calculate a star rating for the dummy food product, modify nutritional information for the dummy food product, and recalculate the star rating.

The invention also includes a method implemented, at least in part, by a computing system, and comprising the steps of maintaining one or more food product information tables, identifying in the one or more tables one or more food products, each by a unique identifier, listing ingredients of the one or more food products, listing nutritional information of the one or more food products, and identifying nutritional value element mapping based on food product nutritional information. The method also includes the steps of designating a rating algorithm type for each food product and determining a nutritional value rating of the food products based on the element mapping and the rating algorithm type. Additionally, the method may include the steps of generating one or more reports displaying nutritional information for one or more of the one or more food products based on selectable nutritional information, generating one or more reports displaying nutritional information and rating information for one or more of the one or more food products based on selectable nutritional rating, generating one or more reports displaying nutritional information and rating information for one or more of the one or more food products based on company name, or grouping the one or more food items based on product state selected from the group consisting of items new to system, items pending for rating, items rated, items flagged do not rate and items ready for rating. Additional steps of the method include, but are not limited to modifying food product ingredient or nutritional information and recalculating nutritional value rating, and setting up a dummy food product in the one or more food product information tables, calculating a star rating for the dummy food product, modifying the nutritional information for the dummy food product, and recalculating the star rating for the dummy food product.

The combination of the relational database and the programming function embodied in software enables a food distributor, food retailer, or any party interested in assessing and evaluating nutritional value information for a wide array of food products in a uniform manner to access that information. This and other advantages of the present invention will become apparent upon review of the following detailed description, the accompanying drawings and the appended claims.

BRIEF DESCRIPTION OF THE DRAWINGS

FIG. 6 is a display of a third screen representing an interface for a user to access the relational database by item identification through the primary section tab View Items.

FIG. 7 is a display of a fourth screen representing an interface for a user to access the relational database by links to items identified through the primary tab search screen of FIG. 5.

FIG. 8 is a display of a fifth screen representing an interface for a user to access information about an item selected by clicking on a link from a list of items of the type shown in FIG. 7.

FIG. 9 is a display of a sixth screen representing a continuation of the interface beginning with the screen shown in FIG.

8, showing the interface for a user to access base nutrients information and access tabs for other nutrient information for the item shown in FIG. 8.

Figure 10:

FIG. 10 is a display of a seventh screen representing an interface for a user to access vitamins information for a selected item.

Figure 11:
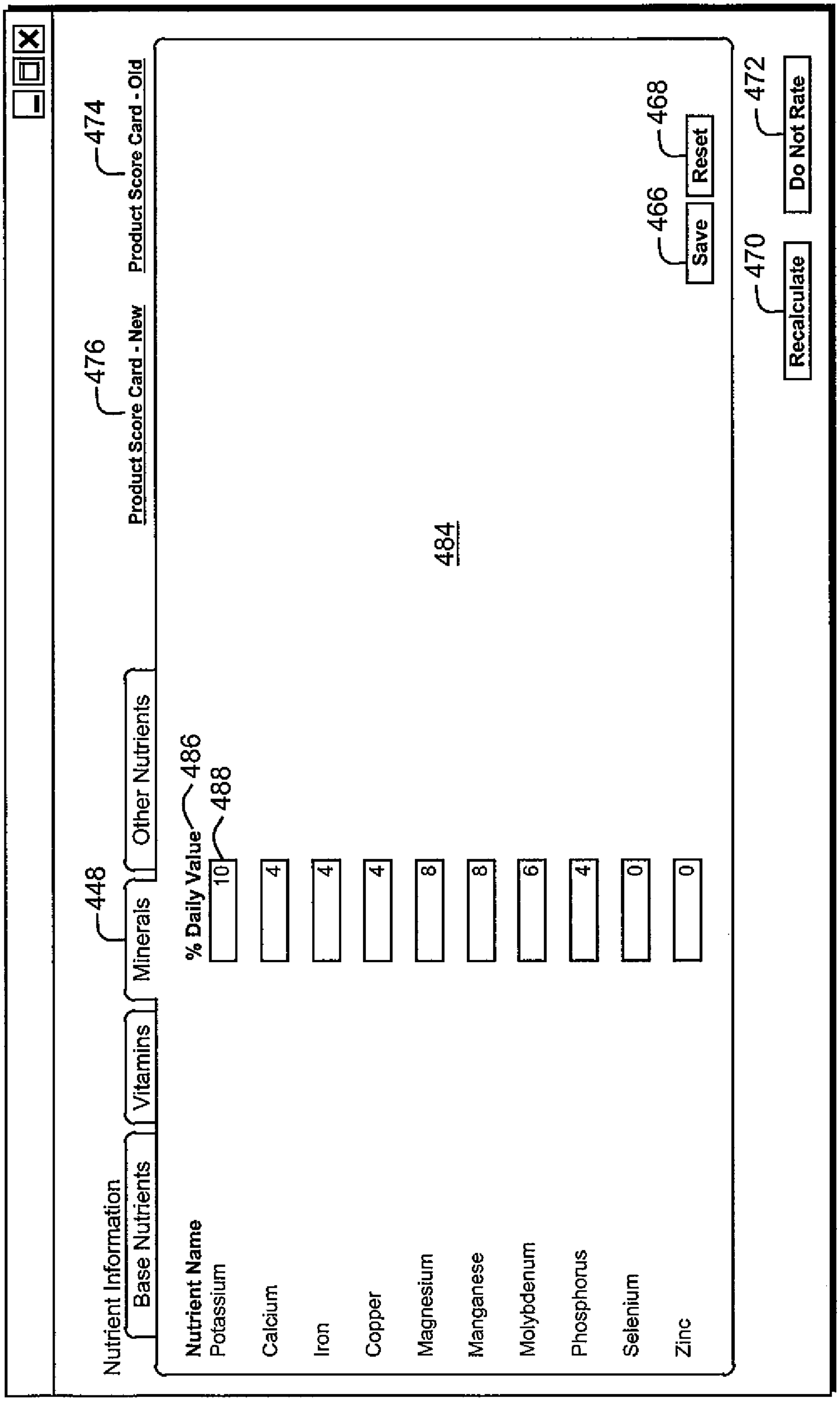

FIG. 11 is a display of an eighth screen representing an interface for a user to access minerals information for a selected item.

FIG. 12 is a display of a ninth screen representing an interface for a user to access other nutrients information for a selected item.

FIG. 13A is a display of a first portion of a tenth screen representing a portion of the information about a food item for which no revised information has been introduced and the star rating has not been recalculated. FIG. 13B is a display of a second portion of the tenth screen representing a remainder of the information about the food item of FIG. 13A for which no revised information has been introduced.

FIG. 14A is a display of a first portion of an eleventh screen representing a portion of the information about the same food item of FIGS. 13A and 13B but for which revised information has been introduced and the star rating recalculated. FIG. 14B is a display of a second portion of the eleventh screen representing a remainder of the information about the food item of FIG. 14A for which revised information has been introduced.

FIG. 15 is a display of a twelfth screen representing an interface for a user to view Super Category information for food items stored in the relational database through activation of the primary section tab View Super Category.

Figure 16:
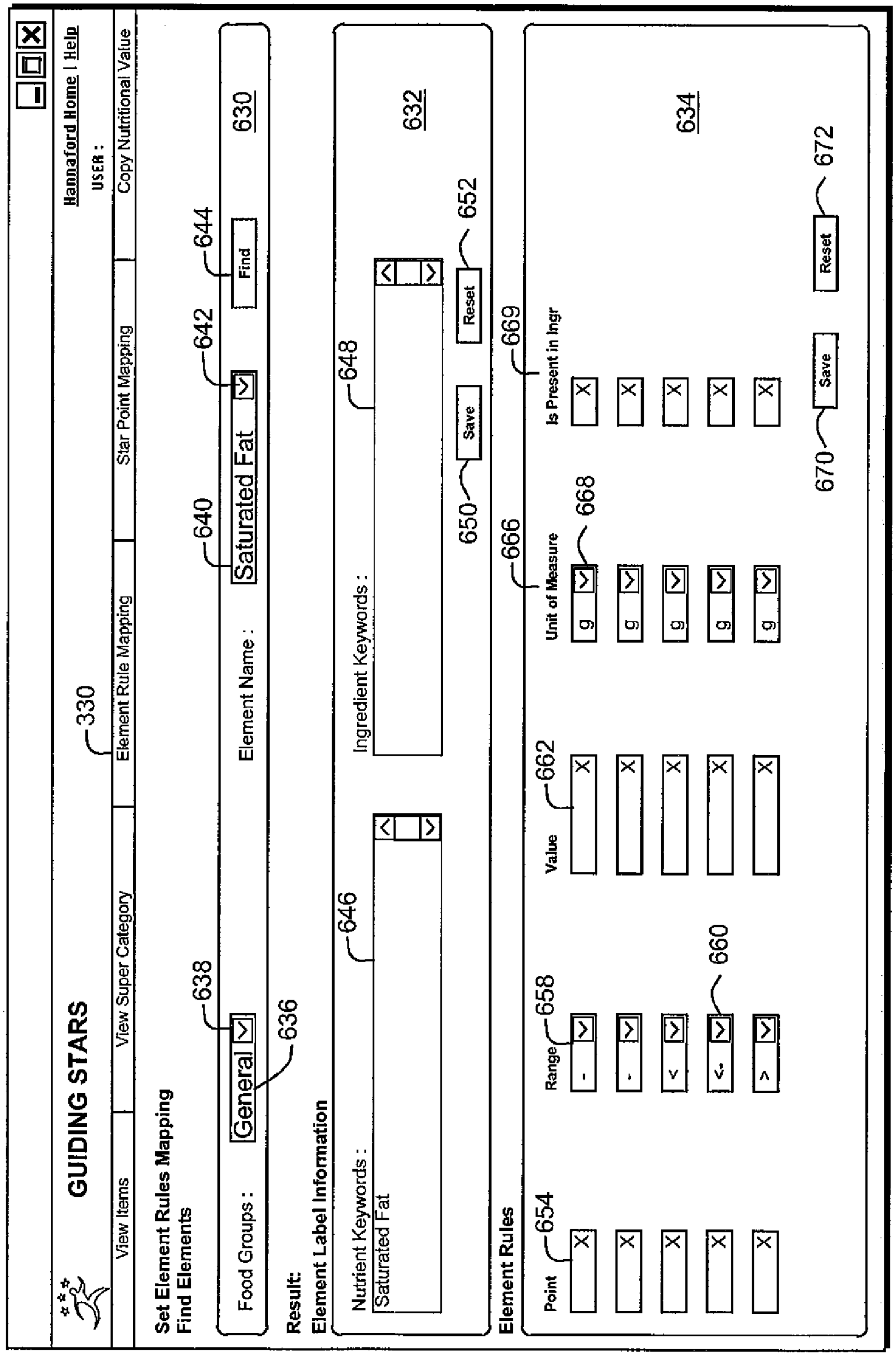

FIG. 16 is a display of a thirteenth screen representing an interface for a user to view, add and/or modify the element valuing rules for item scoring used to establish star ratings through activation of the primary section tab Element Rule Mapping.

FIG. 17 is a display of a fourteenth screen representing an interface for a user to confirm that rules information changes made should be accepted, and further illustrating one example valuation nutrient keywords change, which screen is accessed by activating the Save key of FIG. 16.

Figure 18:
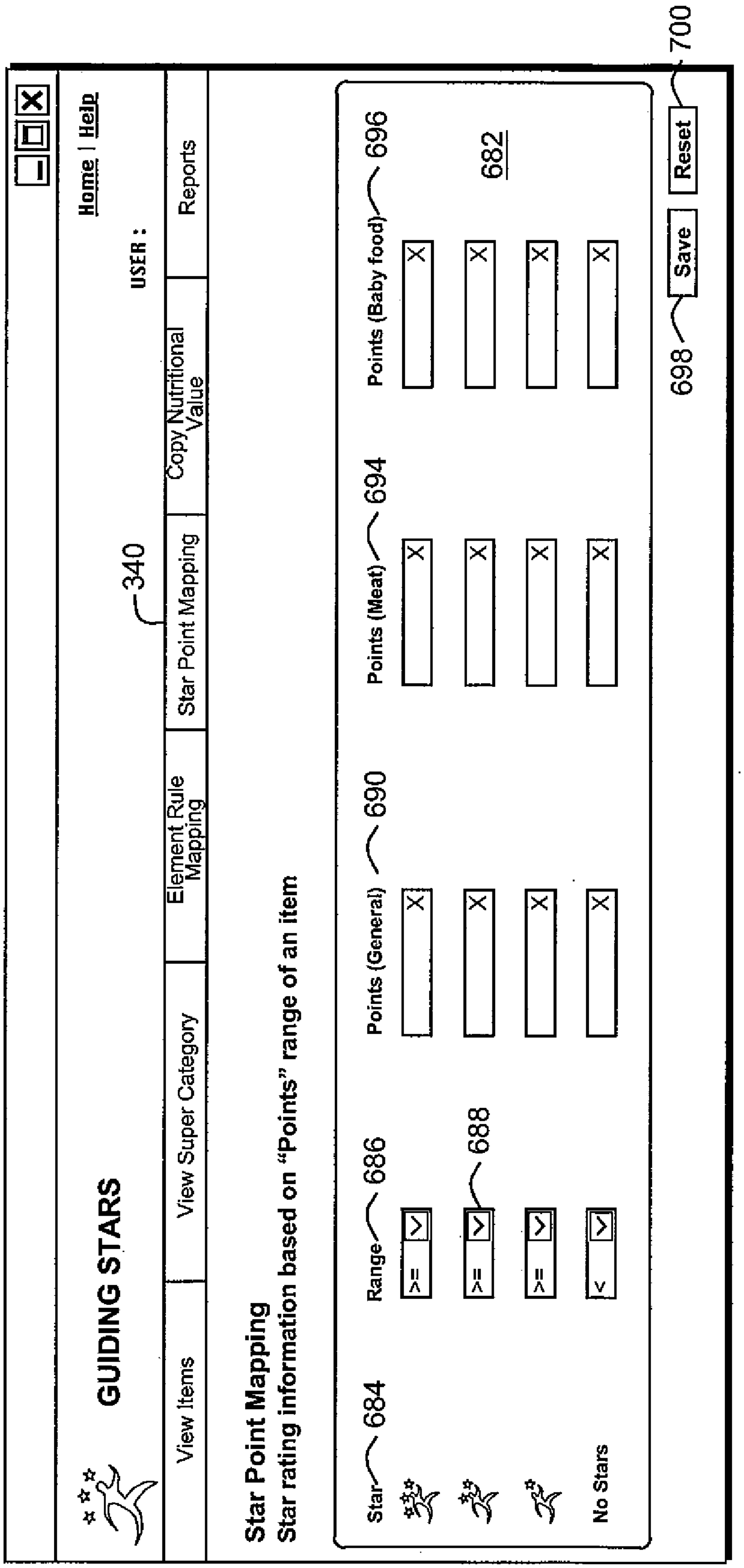

FIG. 18 is a display of a fifteenth screen representing an interface for a user to view and modify the relationship between star ratings and element value totals through the primary section tab Star Point Mapping.

Figure 19:
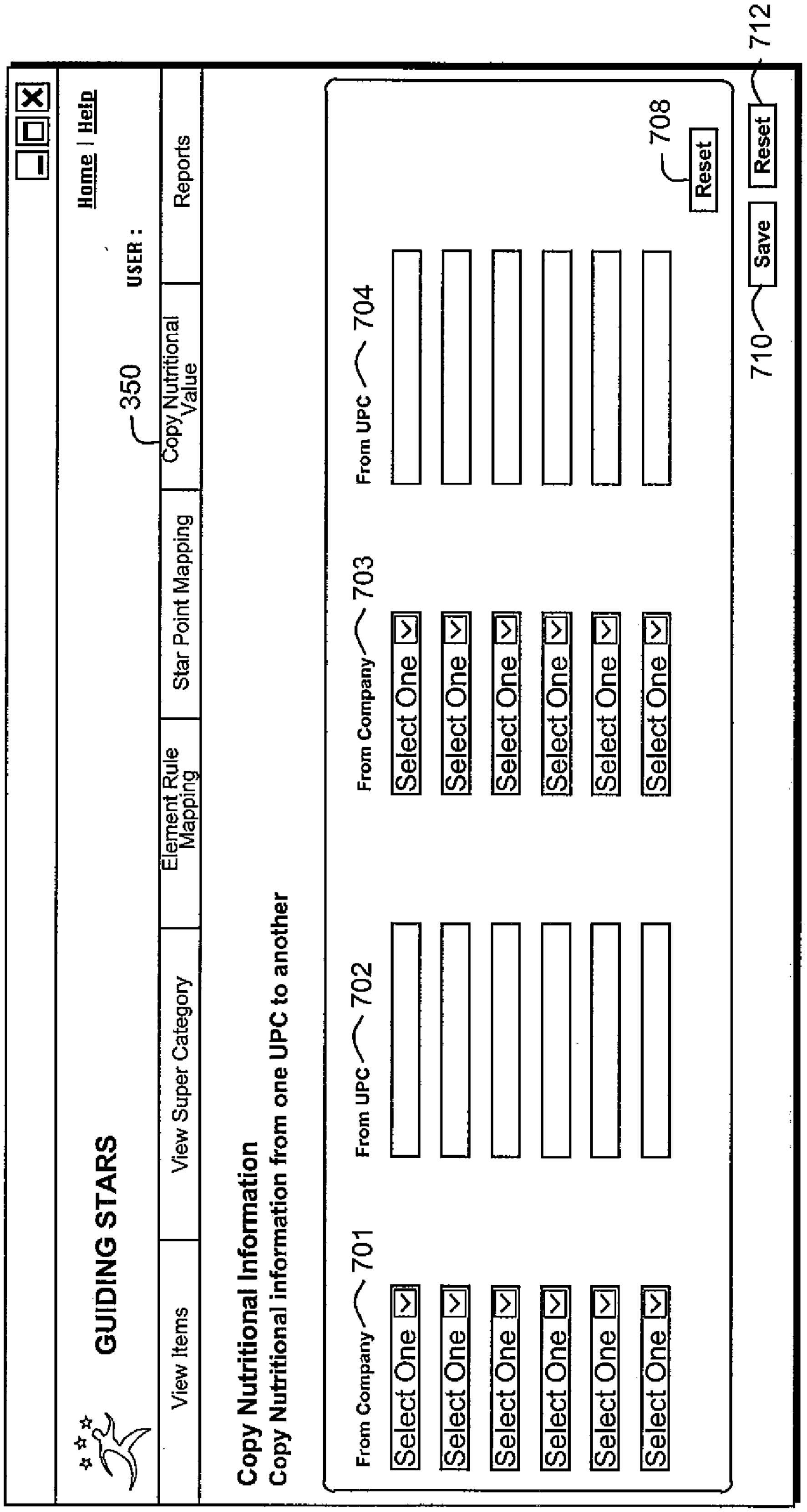

FIG. 19 is a display of a sixteenth screen presenting an interface for a user to copy the information of one or more items to one or more other items through the primary section tab Copy Nutritional Value.

Figure 20:
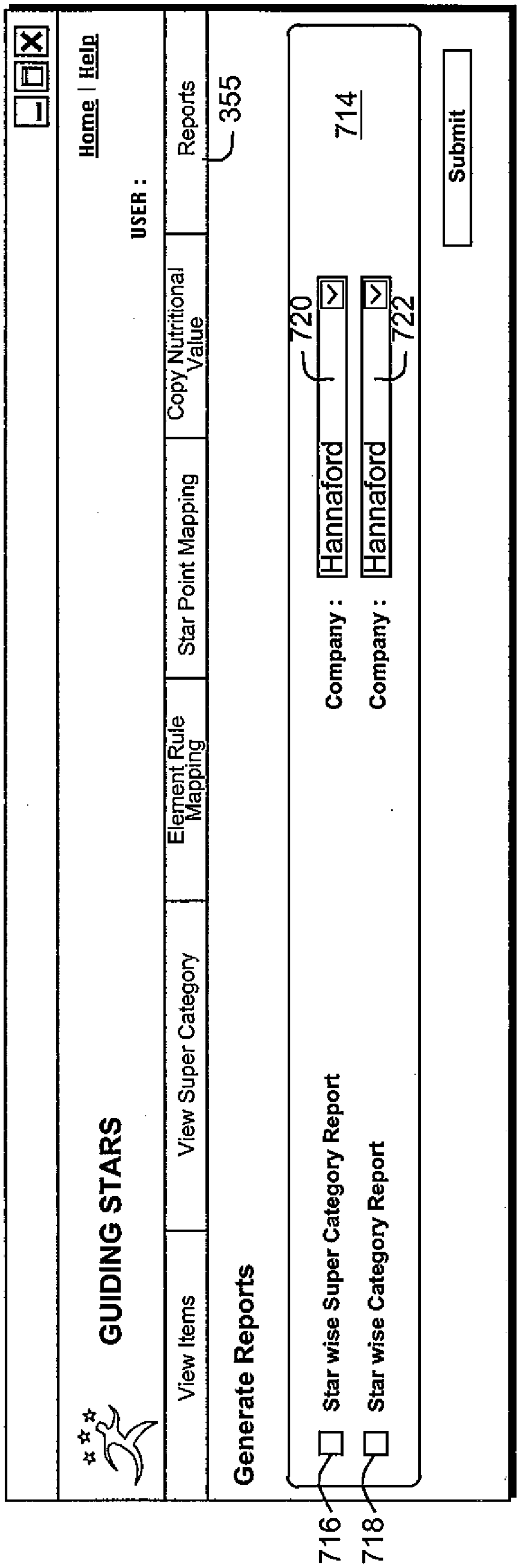

FIG. 20 is a display of a seventeenth screen presenting an interface for a user to generate one or more reports about individual food items, sets of food items, or other information of interest retrievable from the Database.

DETAILED DESCRIPTION OF THE PREFERRED EMBODIMENT

Figure 1:
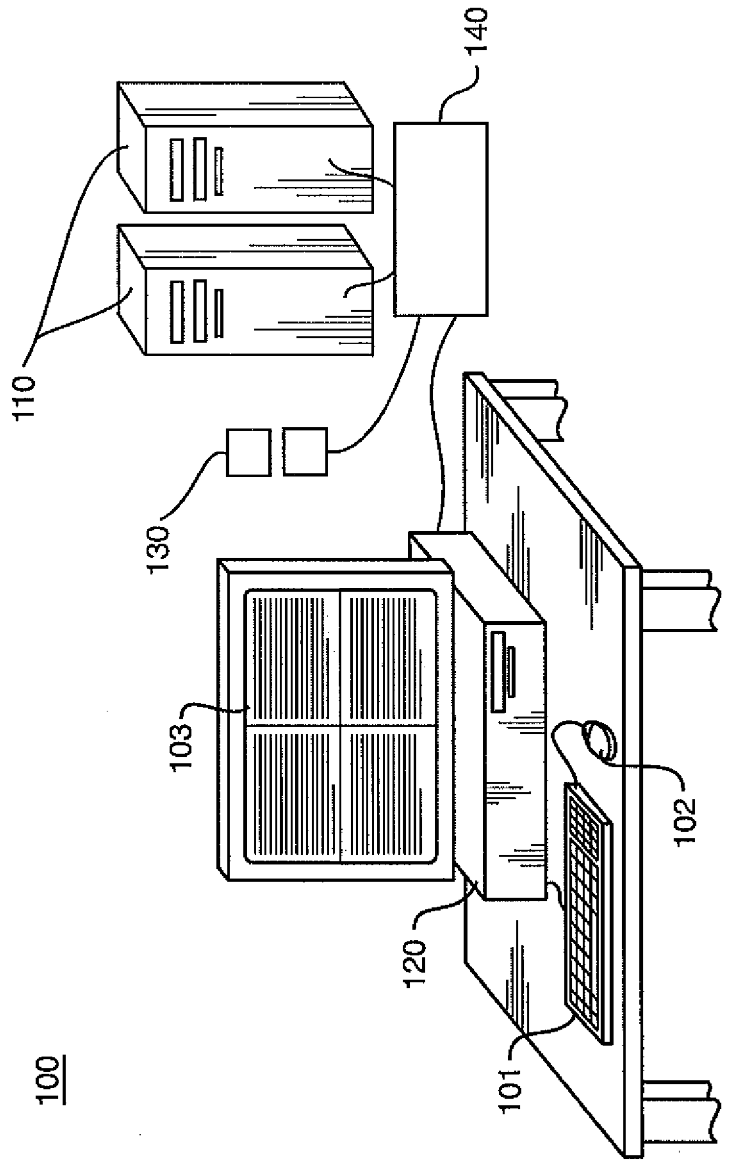
FIG. 1 is a simplified representation of a computing system suitable for carrying out the functions of the present invention as described herein.

The present invention is a system, process and related database for gathering and storing food nutritional information to enable access to that information and to enable manipulation of that information to produce food nutritional value information. The system and database are embodied in a computing system programmed to perform functional steps associated with the storing of the information for the purpose of accessing it and carrying out calculations based on it. Any type of computing system suitable to store information in the amount of interest and to perform calculations of interest on the information may be employed and is represented generally in FIG. 1. The computer system 100 shown is only one example of a suitable computing environment and is not intended to suggest any limitation as to the scope of use or functionality of the invention. For example, the computer system 100 may be associated with local or remote computing means, such as one or more central computers, such as server 110 in a local area network, a metropolitan area network, a wide area network, or through intranet and internet connections.

The computer system 100 may include one or more discrete computer processor devices, represented by desktop computer 120, for example. Examples of well known computing devices that may be suitable for use with the invention include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like. The computer system 100 may include computer devices operated by one or more users, such as through a desktop, laptop, or servers, and/or one or more providers of services corresponding to one or more functions of the invention.

The server 110, the computer processor 120, or a combination of both may be programmed to include one or more of the functions of the invention system. The relational database of the present invention for gathering, storing and making accessible the food nutritional information, is represented by Database 130. For the purpose of the description of the present invention, a database is a collection of stored data that are logically related. Although there are different types of databases, and the Database 130 of the present invention may be any of such types, it is preferably a relational database with a relational database management system, comprising tables made up of rows and columns. Data stored in the relational tables are accessed or updated using database queries submitted to the database system.

Database 130 may be associated with the server 110, the computer processor 120, other computing devices, or any combination thereof, include information related to the use of the invention system. The Database 130 may be associated with a single computing device or a plurality of devices. The Database 130 may be centrally located or it may be distributed locally or widely. The Database 130 is populated and updated with the information to be described herein in a format to be described herein. All of the devices may be interconnected through one or more signal exchange devices, such as router/switch 140.

The invention may be described in the general context of computer-executable instructions, such as program modules, being executed by a computer such as the computer system 100. Generally, program modules include routines, programs, objects, components, data structures, etc. that perform particular tasks or implement particular abstract data types. As indicated above, the system of the present invention may also be practiced in distributed computing environments where tasks are performed by remote processing devices that are linked through a communications network or other data transmission medium. In a distributed computing environment, program function modules and other data may be located in both local and remote computer storage media including memory storage devices.

The computer processor 120 and interactive drives, memory storage devices, databases, including but not limited to the Database 130, and peripherals may be interconnected through one or more computer system buses. The system buses may be any of several types of bus structures including a memory bus or memory controller, a peripheral bus, and a local bus using any of a variety of bus architectures. By way of example, and not limitation, such architectures include Industry Standard Architecture (USA) bus, Micro Channel Architecture (MCA) bus, Enhanced ISA (EISA) bus, Video Electronics Standards Association (VESA) local bus, and Peripheral Component Interconnect (PCI) bus.

The computer system 100 typically includes a variety of computer readable media. Computer readable media can be any available media that can be accessed by computer system 100 and includes both volatile and non-volatile media, removable and non-removable media. By way of example, and not limitation, computer readable media may comprise computer storage media and communication media. Computer storage media includes both volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by the computer system 100.

The computer system 100 further includes computer storage media in the form of volatile and/or non-volatile memory such as Read Only Memory (ROM) and Random Access memory (RAM). RAM typically contains data and/or program modules that are accessible to and/or operated on by computer processor 120. That is, RAM may include application programs, such as the functional modules of the system of the present invention, and information in the form of data. The computer system 100 may also include other removable/non-removable, volatile/non-volatile computer storage and access media. For example, the computer system 100 may include a hard disk drive to read from and/or write to non-removable, non-volatile magnetic media, a magnetic disk drive to read to and/or write from a removable, non-volatile magnetic disk, and an optical disk drive to read to and/or write from a removable, non-volatile optical disk, such as a CD-ROM or other optical media. Other removable/non-removable, volatile/non-volatile computer storage media that can be used in the computer system 100 to perform the functional steps associated with the system and method of the present invention include, but are not limited to, magnetic tape cassettes, flash memory cards, digital versatile disks, digital video tape, solid state RAM, solid state ROM, and the like.

The drives and their associated computer storage media described above provide storage of computer readable instructions, data structures, program modules and other data for the computer processor 120. A user may enter commands and information into the computer processor 120 through input devices such as a keyboard 101 and a pointing device 102, commonly referred to as a mouse, trackball or touch pad. Other input devices (not shown) may include a microphone, joystick, game pad, satellite dish, scanner, or the like. These and other input devices are connected to the computer processor 120 through the system bus, or other bus structures, such as a parallel port, game port or a universal serial bus (USB), but is not limited thereto. A monitor 103 or other type of display device is also connected to the computer processor 120 through the system bus or other bus arrangement. In addition to the monitor 103, the computer processor 120 may be connected to other peripheral output devices, such as printers (not shown). Commands and information may be entered by one or more users any one or more of whom may be located in the same or different locations. Commands and information may be entered at designated or random times.

The computer processor 120 may be configured and arranged to perform functions and steps embodied in computer instructions stored and accessed in any one or more of the manners described. The functions and steps, such as the functions and steps of the implementation of the relational database and its use in regard to the present invention, individually or in combination, may be implemented as a computer program product tangibly as computer-readable signals on a computer-readable medium, such as any one or more of the computer-readable media described. Such computer program product may include computer-readable signals tangibly embodied on the computer-readable medium, where such signals define instructions, for example, as part of one or more programs that, as a result of being executed by the computer processor 120, instruct the computer processor 120 to perform one or more processes or acts described herein, and/or various examples, variations and combinations thereof. Such instructions may be written in any of a plurality of programming languages, for example, XML, Java, Visual Basic, C, or C++, Fortran, Pascal, Eiffel, Basic, COBOL, and the like, or any of a variety of combinations thereof. Information entry may be effected using such programming languages as well as other applications including for example and in no way limited thereto, database programs ACCESS and DB2. The computer-readable medium on which such instructions are stored may reside on one or more of the components described above and may be distributed across one or more such components.

Figure 2:
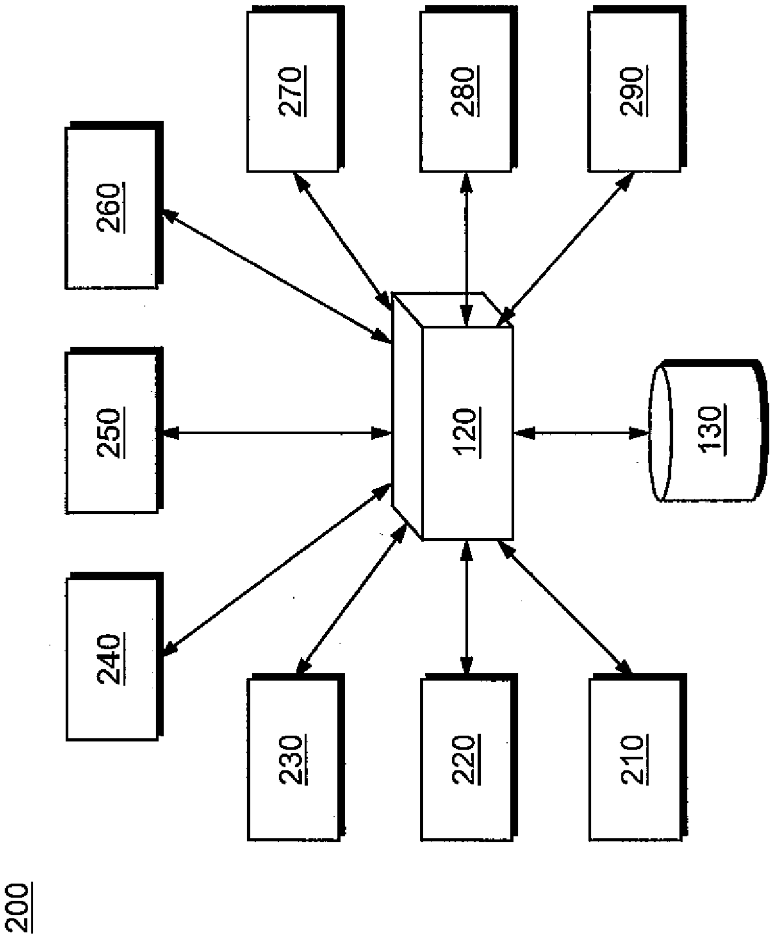
FIG. 2 is a simplified flow diagram representing primary functions of the process of inputting and scoring food product nutritional information in accordance with the purpose of the present invention.

With reference to FIG. 2, an information input and processing system 200 of the present invention includes a plurality of functions embodied in one or more computer programs executable through the computer processor 120 of the computer system 100, wherein signals are exchanged between the functions and the computer processor 120, and between the database 130 and the functions through the computer processor 120. Functions of the system 200 include a local common products information input function 210, a remote common products information input function 220, a local unique products information input function 230, a remote unique products information input function 240, a data input reporting function 250, a nutritional value designation function 260, a remote rating function 270, a local rating function 280 and a tag generation function 290. All or a portion of the identified functions may be employed in carrying out steps to calculate and report food nutritional value and rating information.

The local common products information input function 210 of the system 200 enables a user to input to the Database 130 information for food products that are made available through, or are otherwise of interest to, an entity, such as a food products retailer and that may also be available, or of interest, to another party. Cereal from a commercial manufacturer is one instance of a common food product. In the example of the Guiding Stars$^{SM}$ program created by the assignee of the present application, Hannaford is a food products retailer offering thousands of food items to consumers. In addition, Hannaford may have an affiliation with another food retailer that is located remote from Hannaford and that remote affiliate may share in common with Hannaford the ability to offer to consumers at least a portion of the total number of food products that are offered by Hannaford. As a primary administrator of the system 200 with authorization to access and modify the Database 130, through programming represented by the local common products information input function 210, Hannaford would input food item information into the Database 130 that it offers that is also available through its affiliate. The local common products input function 210 permits the user to identify the original provider of the food product information (Hannaford in the example) as well as the names of one or more others that also provide the same product or products. Of course, the local supplier of the information could be a party of any type and is not intended to be limited to food retailers alone. The Database 130 is arranged to include information designation to tag food products as being of common interest to a plurality of parties.

As with the local common products information input function 210, the remote common products information input function 220 of the system 200 enables a user to input to the Database 130 information for food products that are made available through, or are otherwise of interest to, an entity, such as a food products retailer and that may also be available, or of interest, to another party. However, for this function, the originator of the food product information would not be the party that otherwise controls the Database 130, but instead a party that has an interest in the use of, and some potentially restricted access to, the Database 130. In the example described in the preceding paragraph for the Guiding Stars$^{SM}$ program, it would be the Hannaford affiliate that would generate the food product information, which food product information may be of interest to one or more other parties, such as Hannaford, for example. Of course, the remote supplier of the information could be a party of any type and is not intended to be limited to food retailers alone. The system 200 administrator would obtain the information from the remote information provider and, through programming represented by the remote common products information input function 220, would input food item information into the Database 130 that it also provides or that otherwise is of interest to the Database 130 administrator. The remote common products input function 220 permits the user to identify the original provider of the food product information as well as the names of one or more others that also provide the same product or products.

The local unique products information input function 230 of the system 200 enables a user to input to the Database 130 information for food products that are made available only through a single party and not through others. For example, a food retailer may provide prepared foods with their unique recipes that are available only by one retailer, and possibly by only one store of the retailer. The system 200 administrator associated with the unique food item provider, through programming represented by the local unique products information input function 230, would input food item information into the Database 130 that is offered only by that provider. The local unique products input function 230 permits the user to identify the original provider of the food product information. Of course, the local provider of the information could be a party of any type and is not intended to be limited to food retailers alone. The Database 130 is arranged to include information designation to tag food products as being of unique interest to a specific party.

The remote unique products information input function 240 of the system 200 enables a user to input to the Database 130 information for food products that are made available only through a single party and not through others, wherein the single party is not directly associated with the system 200 administrator. The system 200 administrator, through programming represented by the remote unique products information input function 240, would input food item information into the Database 130 that is offered only by the remote. The remote unique products input function 240 permits the system 200 administrator to identify the original provider of the food product information. Of course, the remote provider of the information could be a party of any type and is not intended to be limited to food retailers alone. Further, it is to be understood that the remote provider may or may not have access to the Database 130. If the remote provider does have such access, its access may be limited to a portion of the contents of the Database 130. For example, the remote provider may only be able to view information regarding its unique food items and those food items it has in common with others for which it is permitted to gain access to.

The information that is provided to the Database 130 through the system 200, whether obtained locally or remotely or from one party or a plurality of parties, includes at least the minimum of: name of the product, Universal Product Code (UPC) as a unique product identification; source of the information; manufacturer of the product; description of the product; product ingredients; and nutritional information. Additional optional information may include, but not be limited to: any warnings listed about the product; the Nutrition Facts Panel, if available; supplemental product information; food product grouping; and food product subgrouping. The source of the food product information may be the original manufacturer, such as through a Nutrition Facts Panel, if one is required. Other sources of food product information include, but are not limited to: public information sources, such as the United States Department of Agriculture; private information sources, such as the ESHA Genesis SQL nutrient database available through ESHA Research of Salem, Oreg.; a food preparer, such as the deli department of a food retailer. The system 200 of the presented invention has been arranged to receive food information in a variety of forms from a variety of sources, and organize that information via the Database 130 into a common format that enables nutritional element valuing and, ultimately, rating of the food product based on the nutritional element valuing. No other food information source provides such functionality.

With continuing reference to FIG. 2, the data input reporting function 250 permits the user to confirm that food product information suitable for nutritional rating has been stored in the Database 130 in a form suitable for generating the rating. The data reporting function 250 also flags items for which the information is insufficient to establish a rating. Further, the data input reporting function 250 includes programming to generate Graphical User Interfaces that enable a user of the system 200 to observe food product information stored in the Database 130 and, for those users with authorization to do so, to modify the food product information contained in the Database 130. Such a change may be made, for example, when a food product provider has changed the ingredients for a named product already having a designated UPC.

The nutritional value designation function 260 is configured through programming to activate the algorithm described in the referenced co-pending application to acquire food product information contained in the Database 130 and perform calculations thereon to generate nutritional value points. The nutritional value designation function 260 performs in conjunction with the local rating function 270 and the remote rating function 280 to produce star rating designations for one or more selected food items contained in the Database 130. Those of ordinary skill in the art will recognize the programming details required to carry out the steps described in the referenced co-pending application to generate the nutritional element valuing and the rating calculations. The nutritional value designation function 260 and the local rating function 270 and the remote rating function 280, in combination, perform the functions of gathering the necessary food nutritional information and the algorithm. Further, the local rating function 270 includes a subfunction to enable the reporting of food ratings for one or more food items of interest to the local provider of the food or the information. The remote rating function 280 includes a subfunction to enable the reporting of food ratings for one or more food items of interest to the remote provider of the food or the information.

The system 200 may be activated for use periodically, regularly, continuously or sporadically. The food product information may be gathered on a regular or sporadic basis. The check of the quality of the information gathered through the data input reporting function 250 may be performed regularly or sporadically. The steps associated with performing food nutritional valuing through the nutritional value designation function 260, and the food nutritional value rating calculations performed through the local rating function 270 and/or the remote rating function 280 may be performed regularly or sporadically. In the example of Hannaford's Guiding Stars$^{SM}$ program, system checks for new data inputs are performed twice weekly and final confirmation of ratings to be calculated are performed twice per week. The confirmation calculations are performed prior to undertaking any steps to generate any materials that may be required to present rating information to consumers. All results produced are preferably retained.

A related optional function of the system 200 that is implemented as part of the Guiding Stars$^{SM}$ program is the tag generation function 290. The tag generation function 290 is an interface between the rating functions 270/280 and a food provider's display tag system used to present summary information to retail food consumers. Specifically, the tag generation function 290 generates information on the star rating for each food item for which a first star rating has been generated, or for which a star rating has been changed, such as resulting from a change of food item nutritional information or a change in the algorithm. That information is transferred to a program or function that is engaged to make tags including the rating information. It is to be understood that the tag generation function 290 may not be required to some types of users of the system 200. For example, a party interested in food product nutritional information for research, reporting or purposes other than providing retail consumer food information at the point of sale, would likely have no need to generate information tags.

The system 200 represented in FIG. 2 may be embodied in one or more computer programs and one or more computer systems. It may be embodied in software, hardware, firmware or any combination thereof. The functions shown may be performed through the computer processor 120 as a single computing mechanism, or through a plurality of computer processors represented by processor 120. The system 200 may include one or more embodiments of the Database 130, which Database 130 may be embodied in the computer processor 120 or in one or more other computer systems in electronic communication with the computer processor 120. It is to be noted that information gathered, stored and/or manipulated through the system 200, may be used without specific presentation on a graphical user interface of the computer system 100. For example, the output of information may be transferred among computer devices, or within a networked computing system, without specific presentation on a display.

As indicated herein, the Database 130 stores all food nutritional information in original and adjusted form, as well as any information of interest related to the food products for which nutritional information is gathered, and the information output based on implementation of the food nutritional value scoring or such other manipulation of the gathered and stored information. FIGS. 3A-3D in combination show a view of an embodiment of a format of the Database 130 in which each box is a table and each table includes a set of entities or fields. Entities represent data that describe characteristics of a food product. For example, the table PRDT_INFO includes, but is not limited to, entities of product brand name, product generic name, and product weight. 12

Relationships: The lines between tables reflect the relationship between two or more entities. Note that one end of the line can be straight, which means that there is a one-to-one relationship to the particular table, while the other end of the line is a representation of a key, which means a many-to-one relationship. For example, the relationship between the PRDT_INFO table and the RECIPE table. The end of the line connecting to the PRDT_INFO table is straight while its opposing end has a key connecting to the RECIPE table. This means that one set of product information can be used in many recipes. A dashed line means that primary key entities of one table are embodied in data associated with another table to which the dashed line is linked. A solid line means that primary key entities of one table are also primary key entities of another table to which the solid line is linked.

Description of tables in FIGS. 3A-3D: FIGS. 3A-3D include a set of diagrams of the tables and entities in the Database 130. The table names and their descriptions are as follows.

PROD_INFO: This table has product level information

PRDT_LBL: This table has information at food product provider (such as original supplier, distributor or retailer) level for a particular product.

RECIPE: This table stores information on the different preparations possible for the product. (E.g. cereals can be served dry or with milk etc.) Each preparation will have a record in this table.

PRDT_NUTRI: This table stores information on the quantity or percentage of a nutrient in a product for a specific preparation. This information is obtained from the Nutrition Facts panel on the label.

NUTRI_MSTR: This table stores the information on all the master nutrients that might be present in a product.

ELEMENTS: This table stores the information of the major elements that are required to calculate the rating of a product based on its food group. The different food groups are General, Meat, Baby food and Fats & Oils.

ELE_PNT: This table stores the information of different rules and points mapping to calculate the nutritional value star rating of the product.

SUB _ELE: This table stores the information of mapping of different major elements and their subelements.

EXCP_MSTR: This table stores the type of information missing from the product information that would result in generating a decision not to rate that product.

EXCP: This table stores the information of specific exceptions available under the EXCP_MSTR catalog that are associated with a specific product that would render that product not ratable. COMPANY: This table stores the information of different product information providers.

PRD_CAT: This table stores the information of all the product categories present in the Database 130.

SEQ_CNTL: This table is used to store the control designations for sequencing the functions of the tables of the Database 130 and to determine whether product rating recalculation or new calculation is required.

Tables 1-13 provide details about the entities associated with the tables. Each entity is represented by Type, whether related as a Primary Key and/or a Foreign Key, and a brief description of the information to be included for that entity. The Type is the form of the information, whether an alphabetical character, a numerical character, a fixed character or a variable character. An entity that is a Primary Key entity has one and only one value for its use as part of a particular table. As a first example, the SID_NBR entity for the logical sequence number of a product has a unique value that is consistent throughout the tables. As a second example, the LBL_DSC entity for the product description can have mor e than one value within a table and across tables. An entity that is a Foreign Key links entities, tables or entities and tables together. As an example, the CO_ID—CD entity is common among tables PRDT_LBL and PRDT_CAT for table COMPANY.

TABLE 1

PRDT_INFO

| Entity | Type | Primary Key | Foreign Key | Entity Description |
|---|---|---|---|---|
| SID_NBR | INTEGER | Yes | No | A Logical Sequence Number representing a Product |
| PRDT_LBL_DSC | VARCHAR(150) | No | No | Description of the Product |
| BRND_NAM | CHAR(80) | No | No | Brand name |
| MFR_NAM | VARCHAR(255) | No | No | Manufacturer name |
| RECIP_CNT | SMALLINT | No | No | Count of recipe |
| PRDT_AMT | DECIMAL(7.2) | No | No | Product weight |
| PRDT_UOM_CD | CHAR(10) | No | No | Product Unit of Measure |
| PRDT_LBL_DET_TXT | VARCHAR(4096) | No | No | Detailed description of the Product |
| PRDT_LBL_INGR_TXT | VARCHAR(4096) | No | No | Ingredient text of the Product |
| PRDT_LBL_WARN_TXT | VARCHAR(4096) | No | No | Warning text (if any) for the Product |
| PRDT_PNT_QTY | SMALLINT | No | No | Product Rating Points |
| PRDT_RATG_CD | CHAR(1) | No | No | Product Star Rating |
| CALC_FLG | CHAR(1) | No | No | Flag Indicating whether Product needs to be rated or not |
| RATG_EFF_DT | DATE | No | No | Date from which rating of the Product is effective |
| PRDT_SCR_CD | CHAR(1) | No | No | Source from which Product nutritional information is sourced |
| SRC_SENT_TS | TIMESTMP | No | No | Date on which Product is moved from New to Pending |
| POST_DT | DATE | No | No | Date on which Product is moved from Pending to Ready for rating |
| PRDT_ALG_FLG | CHAR(1) | No | No | Algorithm flag under which Product is rated |
| ADD_USER_ID | CHAR(20) | No | No | Add user identification |
| ADD_TS | TIMESTMP | No | No | Add time stamp |
| MOD_USER_ID | CHAR(20) | No | No | Modified user identification |
| MOD_TS | TIMESTMP | No | No | Modified time stamp |

TABLE 2

PRDT_LBL

| Entity | Type | Primary Key | Foreign Key | Entity description |
|---|---|---|---|---|
| SID_NBR | INTEGER | Yes | Yes | A Logical Sequence Number representing a Product |
| UPC_NBR | DECIMAL(14.0) | Yes | No | UPC number of the Product |
| CO_ID_CD | CHAR(5) | Yes | Yes | Company of the Product |
| SUPER_CATG_ID | CHAR(5) | No | Yes | Supercategory identification to which Product belongs |
| MJR_CATG_ID | CHAR(5) | No | Yes | Major category identification to which Product belongs |
| INTMD_CATG_ID | CHAR(5) | No | Yes | Intermediate Category identification to which Product belongs |
| MNR_CATG_ID | CHAR(5) | No | No | Minor Category identification to which Product belongs |
| ITEM_NBR | DECIMAL(14.0) | No | No | Item number of the Product |
| ITEM_CHK_DGT_NBR | DECIMAL(1.0) | No | No | Item check digit Number. It is usually 0 |
| OVRD_CD | CHAR(1) | No | No | Flag indicating whether Product is marked Do Not Rate |
| CRT_DT | DATE | No | No | Date on which Product was received for entering nutrient information |
| SRC_STAT_CD | CHAR(1) | No | No | Status of the Product<br>N - New<br>P - Pending<br>R - Rated<br>D With calc Flag as Y - ready for rating<br>D With calc Flag as N - Item with No info<br>X - Discontinued Item |

TABLE 2-continued

PRDT_LBL

| Entity | Type | Primary Key | Foreign Key | Entity description |
|---|---|---|---|---|
| PRDT_ALG_FLG | CHAR(1) | No | No | Algorithm flag sent by the company |
| ITEM_DSC | CHAR(40) | No | No | Description of the Product sent by the company |
| ITEM_CRT_DT | DATE | No | No | Date Product was setup in the origination source prior to initiating the rating process |
| PLU_FLG | CHAR(1) | No | No | Flag indicating whether Product is company specific or carried by others |
| NOTE_TXT | VARCHAR(50) | No | No | Tracking note |
| ADD_USER_ID | CHAR(20) | No | No | Add user identification |
| ADD_TS | TIMESTMP | No | No | Add time stamp |
| MOD_USER_ID | CHAR(20) | No | No | Modified user identification |
| MOD_TS | TIMESTMP | No | No | Modified time stamp |

TABLE 3

RECIPE

| Entity | Type | Primary Key | Foreign Key | Entity Description |
|---|---|---|---|---|
| RECIP_TYP_NBR | SMALLINT | Yes | No | Recipe type number |
| SID_NBR | INTEGER | Yes | Yes | A Logical Sequence Number representing a Product |
| ADD_PRDT_NAM | CHAR(50) | No | No | Additional Product name |
| SRVG_SZ_DSC | CHAR(50) | No | No | Serving size |
| SRVG_SZ_UOM_DSC | CHAR(50) | No | No | Serving size unit of measure |
| SRVG_PER_CTNR_DSC | CHAR(100) | No | No | Serving size per container |
| ADD_USER_ID | CHAR(20) | No | No | Add user identification |
| ADD_TS | TIMESTMP | No | No | Add time stamp |
| MOD_USER_ID | CHAR(20) | No | No | Modified user identification |
| MOD_TS | TIMESTMP | No | No | Modified time stamp |

TABLE 4

PRDT_NUTRI

| Entity | Type | Primary Key | Foreign Key | Entity Description |
|---|---|---|---|---|
| RECIP_TYP_NBR | SMALLINT | Yes | Yes | Recipe type number |
| NUTRI_ID_NBR | SMALLINT | Yes | Yes | Nutrient identification |
| SID_NBR | INTEGER | Yes | Yes | A Logical Sequence Number representing a Product |
| NUTRI_QTY | DECIMAL(7.2) | No | No | Quantity of the Nutrient |
| NUTRI_UOM_CD | CHAR(10) | No | No | Nutrient unit of measure |
| NUTRI_PCT | SMALLINT | No | No | Nutrient percentage |
| ADD_USER_ID | CHAR(20) | No | No | Add user identification |
| ADD_TS | TIMESTMP | No | No | Add time stamp |
| MOD_USER_ID | CHAR(20) | No | No | Modified user identification |
| MOD_TS | TIMESTMP | No | No | Modified time stamp |

TABLE 5

NUTRI_MSTR

| Entity | Type | Primary Key | Foreign Key | Entity description |
|---|---|---|---|---|
| NUTRI_ID_NBR | SMALLINT | Yes | No | Nutrient identification |
| NUTRI_NAM | CHAR(150 | No | No | Nutrient name |
| NUTRI_TYP_CD | SMALLINT | No | No | Nutrient type |
| ADD_USER_ID | CHAR(20) | No | No | Add user identification |

TABLE 5-continued

NUTRI_MSTR

| Entity | Type | Primary Key | Foreign Key | Entity description |
|---|---|---|---|---|
| ADD_TS | TIMESTMP | No | No | Add time stamp |
| MOD_USER_ID | CHAR(20) | No | No | Modified user identification |
| MOD_TS | TIMESTMP | No | No | Modified time stamp |

TABLE 6

ELEMENTS

| Entity | Type | Primary Key | Foreign Key | Entity Description |
|---|---|---|---|---|
| ELE__ITEM__TYP__CD | SMALLINT | Yes | No | Indicate the Element group type |
| ELE__ID__NBR | SMALLINT | Yes | No | Element identification number |
| ELE__NAM | CHAR(25) | No | No | Element name |
| ADD__USER__ID | CHAR(20) | No | No | Add user identification |
| ADD__TS | TIMESTMP | No | No | Add time stamp |
| MOD__USER__ID | CHAR(20) | No | No | Modified user identification |
| MOD__TS | TIMESTMP | No | No | Modified time stamp |

TABLE 7

ELE__PNT

| Entity | Type | Primary Key | Foreign Key | Entity Description |
|---|---|---|---|---|
| ELE__ITEM__TYP__CD | SMALLINT | Yes | Yes | Indicate the Element group type |
| ELE__ID__NBR | SMALLINT | Yes | Yes | Element identification number |
| ELE__PNT__IDX__NBR | SMALLINT | Yes | No | Element point index number |
| ELE__PNT__VAL__QTY | SMALLINT | No | No | Point for Element |
| ELE__PNT__OPRTR__CD | SMALLINT | No | No | ID for Operator Code (“0”, “<”)(“1”, “<=”); (“2”, “=”); (“3”, “>”); (“4”, “>=”); |
| ELE__LMT__AMT | DECIMAL(8.2) | No | No | Maximum limit for Element points |
| ELE__UOM__CD | CHAR(10) | No | No | Unit of measure code for Element |
| MIN__NUTRI__QTY | SMALLINT | No | No | Minimum Nutrient quantity |
| ADD__USER__ID | CHAR(20) | No | No | Add user identification |
| ADD__TS | TIMESTMP | No | No | Add time stamp |
| MOD__USER__ID | CHAR(20) | No | No | Modified user identification |
| MOD__TS | TIMESTMP | No | No | Modified time stamp |

TABLE 8

SUB__ELE

| Entity | Type | Primary Key | Foreign Key | Entity Description |
|---|---|---|---|---|
| SUB__ELE__ID | CHAR(50) | Yes | No | Sub Element identification |
| ELE__ITEM__TYP__CD | SMALLINT | Yes | Yes | Indicate the Element group type |
| ELE__ID__NBR | SMALLINT | Yes | Yes | Element identification number |
| SUB__ELE__TYP__CD | SMALLINT | Yes | No | Sub element type code- Nutrient keyword or Ingredient Keyword |
| ADD__USER__ID | CHAR(20) | No | No | Add user identification |
| ADD__TS | TIMESTMP | No | No | Add time stamp |
| MOD__USER__ID | CHAR(20) | No | No | Modified user identification |
| MOD__TS | TIMESTMP | No | No | Modified time stamp |

TABLE 9

EXCP__MSTR

| Entity | Type | Primary Key | Foreign Key | Entity Description |
|---|---|---|---|---|
| EXCP__TYP__ID | SMALLINT | Yes | No | Exception type identification |
| EXCP__TYP__DSC | CHAR(100 | No | No | Exception type description |
| ADD__USER__ID | CHAR(20) | No | No | Add user identification |

TABLE 9-continued

EXCP__MSTR

| Entity | Type | Primary Key | Foreign Key | Entity Description |
|---|---|---|---|---|
| ADD__TS | TIMESTMP | No | No | Add time stamp |
| MOD__USER__ID | CHAR(20) | No | No | Modified user identification |
| MOD__TS | TIMESTMP | No | No | Modified time stamp |

TABLE 10

| EXCP | | | | |
|---|---|---|---|---|
| Entity | Type | Primary Key | Foreign Key | Entity Description |
| EXCP_SID_NBR | INTEGER | Yes | No | A Logical Sequence Number representing Exception occurred |
| UPC_NBR | DECIMAL(14.0) | Yes | No | UPC number of the Product |
| CO_ID_CD | CHAR(5) | Yes | No | Company of the Product |
| EXCP_TYP_ID | SMALLINT | Yes | No | Exception type identification |
| BRND_NAM | CHAR(80) | No | No | Brand name |
| SUPER_CATG_ID | CHAR(5) | No | No | Supercategory identification to which Product belongs |
| MJR_CATG_ID | CHAR(5) | No | No | Major category identification to which Product belongs |
| INTMD_CATG_ID | CHAR(5) | No | No | Intermediate Category identification to which Product belongs |
| MNR_CATG_ID | CHAR(5) | No | No | Minor category of the Product |
| EXCP_MSG | CHAR(150) | No | No | Exception message |
| TABL_NAM | CHAR(25) | No | No | Table name |
| SCR_FILE_CD | CHAR(1) | No | No | Source file code |
| SCR_UPC_DSC | VARCHAR(4096) | No | No | UPC description |
| ADD_USER_ID | CHAR(20) | No | No | Add user identification |
| ADD_TS | TIMESTMP | No | No | Add time stamp |
| MOD_USER_ID | CHAR(20) | No | No | Modified user identification |
| MOD_TS | TIMESTMP | No | No | Modified time stamp |

TABLE 11

| COMPANY | | | | |
|---|---|---|---|---|
| Entity | Type | Primary Key | Foreign Key | Entity description |
| CO_ID_CD | CHAR(5) | Yes | No | Company identification code |
| CO_SCDRY_CD | CHAR(2) | No | No | Company secondary code used in ESHA load |
| CO_PRI_NBR | INTEGER | No | No | Priority of the company for rating the Product |
| CO_DESC | VARCHAR(20) | No | No | Description of the company |
| ADD_USER_ID | CHAR(20) | No | No | Add user identification |
| ADD_TS | TIMESTMP | No | No | Add time stamp |
| MOD_USER_ID | CHAR(20) | No | No | Modified user identification |
| MOD_TS | TIMESTMP | No | No | Modified time stamp |

TABLE 12

| PRDT_CAT | | | | |
|---|---|---|---|---|
| Entity | Type | Primary Key | Foreign Key | Entity Description |
| CO_ID_CD | CHAR(5) | Yes | Yes- | Company identification code |
| SUPER_CATG_ID | CHAR(5) | Yes | No | Supercategory identification to which Product belongs |
| MJR_CATG_ID | CHAR(5) | Yes | No | Major category identification to which Product belongs |
| INTMD_CATG_ID | CHAR(5) | Yes | No | Intermediate category identification to which Product belongs |
| SUPER_CATG_DSC | CHAR(40) | No | No | Supercategory description |
| MJR_CATG_DSC | CHAR(40) | No | No | Major Category description |
| INTMD_CATG_DSC | CHAR(40) | No | No | Intermediate category description |
| PA_ASSC_NAM | CHAR(40) | No | No | Pricing analyst of the Product |
| CM_ASSC_NAM | CHAR(40) | No | No | Category Manager of the Product |
| ADD_USER_ID | CHAR(20) | No | No | Add user identification |
| ADD_TS | TIMESTMP | No | No | Add time stamp |
| MOD_USER_ID | CHAR(20) | No | No | Modified user identification |
| MOD_TS | TIMESTMP | No | No | Modified time stamp |

TABLE 13

| SEQ_CNTL | | | | |
|---|---|---|---|---|
| Entity | Type | Primary Key | Foreign Key | Entity Description |
| SEQ_CNTL_ID | CHAR(2) | Yes | No | Sequence control identification |
| SEQ_CNTL_DSC | CHAR(40) | No | No | Sequence control description |
| SEQ_CNTL_NBR | INTEGER | No | No | Sequence control number |
| ADD_USER_ID | CHAR(20) | No | No | Add user identification |
| ADD_TS | TIMESTMP | No | No | Add time stamp |
| MOD_USER_ID | CHAR(20) | No | No | Modified user identification |
| MOD_TS | TIMESTMP | No | No | Modified time stamp |

There are three major computer program components used to implement the system and access to and usage of the Database 130. They are: 1) the Database 130 schema; 2) a Graphical User Interface (GUI); and 3) a Dynamic Link Library (DLL) that interfaces between the Database 130 and the GUI. In one embodiment, the Database 130 schema is defined in a file established in DB2. In an alternative embodiment, the Database 130 schema may be defined in a file established in Microsoft SQL Server Transact-SQL code. Those of ordinary skill in the art will recognize that other programming means may be employed to establish the Database 130 schema represented schematically in the accompanying drawings and associated written description of the Database 130 design and architecture. The GUI is defined in a file established in Java Server Pages (JSP), Hyper Text Markup Language (HTML) code, and JavaScript code. In this embodiment, the majority of the files for the User Interface are written manually and compiled on a server using a JAVA compiler to create HTML pages. Those of ordinary skill in the art will recognize the specific programming required to generate the GUI as represented in accompanying FIGS. 4-20. The present invention is not limited to the specific programming languages identified herein.

The DLL provides a programmatic interface between the Database 130 and the GUI. The DLL is preferably implemented in JAVA but is not limited thereto. The files of the DLL may be generated manually or they may be compiled using the Java compiler language to examine the other files including, but not limited to, JAVA, which may then be used to generate the JAVA class files. The programming necessary to establish the DLL suitable for linking the Database 130 to the GUI may be prepared by one of ordinary skill in the art based on the detailed information provided herein for the tables and entities and through the GUI screen captures and associated text also provided herein.

In the Hannaford Guiding Stars$^{SM}$ embodiment of the present invention, the system 200 conducts batch processing of food item information through specific arrangements of the functions identified in FIG. 2. The information acquired from external sources and generated by the user are batched for acceptance as part of a first job set. Acquired and any additional information developed are then batched for entry into the Database 130 as part of a second job set. Processing of gathered information to conduct nutritional value scoring and star ratings are batched together as part of a third job set. Reports of nutritional information and scoring and rating are batched together as part of a fourth job set. Tagging instructions are batched together as part of a fifth job set. Optionally, preparation of gathered and calculated information for the purpose of transfer to external sites is batched together as part of a sixth job set. Details of the functions associated with these example batch job sets are provided herein with respect to GUIs to be observed by users of the system 200. More generally, it is to be understood that the particular batching arrangements listed herein with respect to the Hannaford Guiding Stars$^{SM}$ program are intended to be example representations. Others of ordinary skill in the art will recognize that the data acquisition, storage, manipulation and use may be performed using the same or similar functions in different ways without deviating from the primary concepts of the system 200.

With reference to FIGS. 4-20, the products information input functions 210, 220, 230 and 240 of the system 200 enable a user to view, input and adjust food product information, and then to have calculated a food nutritional value rating, which information is also viewable and storable in the Database 130. FIGS. 4-20 are graphical representations of the screens viewed by the user in the food product nutritional information input, rating calculation and storage process. The system 200 embodied in a food nutritional value computer program as described herein, is activated or launched by clicking on an icon representing the program, or otherwise initiating application opening through desktop activation methods well known to users of computer programs. Access to the system 200 and the Database 130 may be regulated by conventional authentication and access rules, such as by the particular role of the user seeking access to the system 200. For example, the system 200 may be arranged to grant full access for modification of food item nutritional information, element rule mapping modifications and star valuing algorithm adjustments. Alternatively, a user may be granted access solely to observe stored information, and calculate element values and star ratings. Other role types and access restrictions may be established and changed from time to time based on guidelines established by the system 200 owner.

Figure 4:
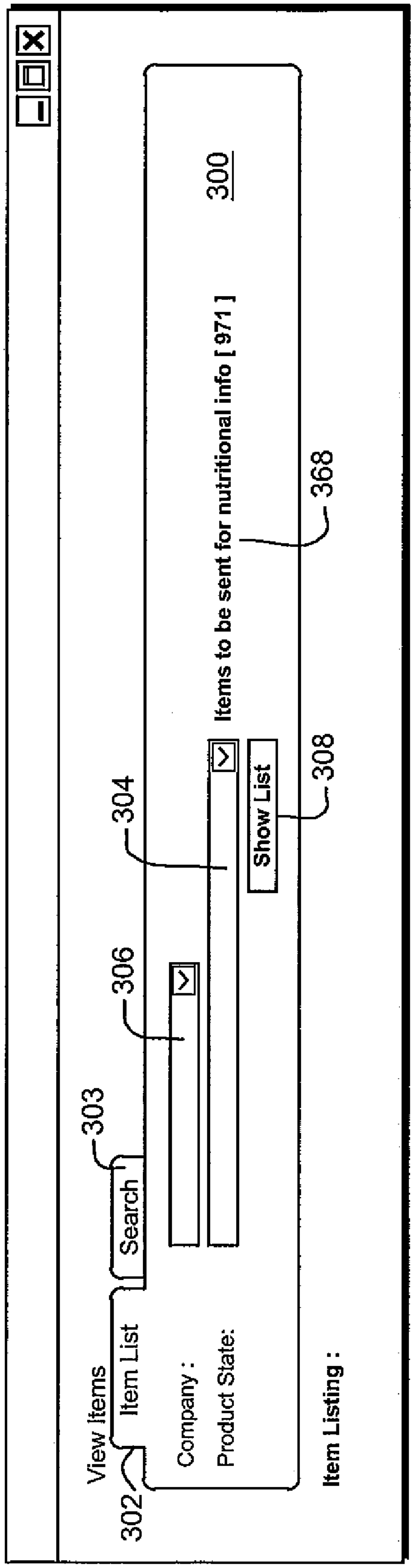
FIG. 4 is a display of a first screen representing the initial interface for a user to access the relational database of the present invention.

Upon activating the system 200, the computer processor 120 enables the user to observe on display 103 a first screen as shown in FIG. 4. The first screen, as with all other screens created through use of the system 200, is a GUI, which enables the user to see one or more interactive display representations of tables and entities of the Database 130, and to manipulate the content of the Database 130 through user inputs, generally either with keystrokes of the keyboard 101, and/or clicking or clicking and dragging with the mouse 102 icons, categories, items, elements, formulas, and the like represented on the display 103.

The initial system access display represented in FIG. 4 presents the user with a simple set of choices for entry into the system 200, which, when activated, enable the user to choose from an array of paths to view and input food information. The GUI of the initial screen includes an initiation tab set 300. The initiation tab set 300 includes an Items List tab 302 and a Search tab 303. The Item List tab 302 includes a Product State drop down menu 304, which gives the user the choice of categorizing food items for display based upon selectable product state parameters. In one embodiment of the present invention, the selectable product state parameters selectable through the Product State drop down menu 304 include "Items new to system", "Items pending for rating," "Items rated," "Items flagged do not rate," and "Items ready for rating." More or fewer selection parameters may be used as desired. The Item List tab 302 further includes a Company drop down menu 306, which gives the user the choice of focusing the search on food items of interest to, or manufactured or sold by, a particular party (designated herein as a Company). Clicking on Show List button 308 triggers the population of a table comprising a list of items matching the Company and Product State parameters selected by the user and shown in one example form in FIG. 6.

Figure 4A:
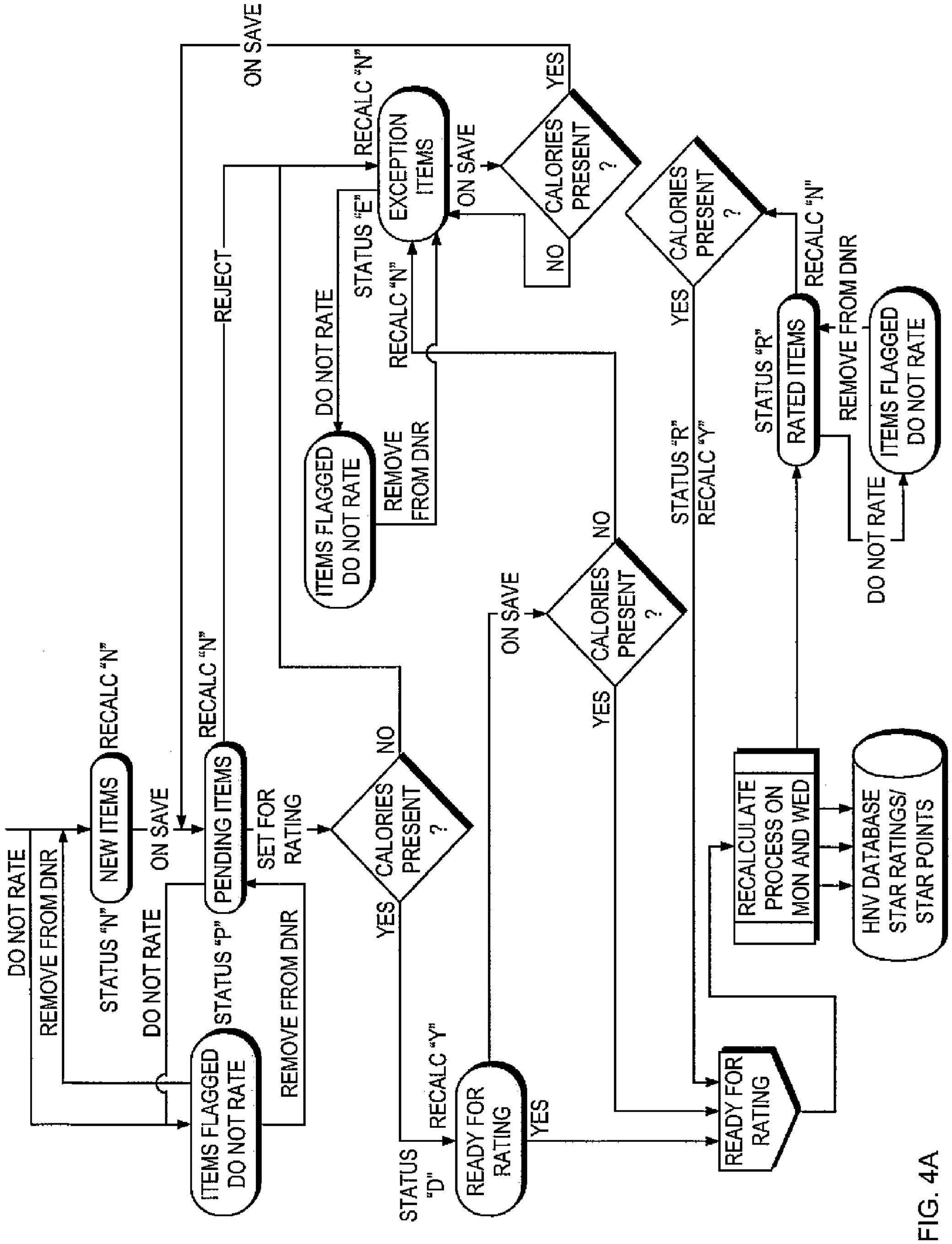
FIG. 4A is a simplified flow diagram of the process for designating food product state.

A simplified representation of the flow of decision making for the product state designations is shown in FIG. 4A, wherein DNR stands for "do not rate." The decision making process carried out by the system 200 such as through at least functions 210-240, involves first determining whether all information required to establish a rating for a food item is available for that item. If not, or if the particular item is the type that should not be rated (including, for example, a non-food item), the item is flagged as do not rate. Such items may either be removed from the Database 130 or they may be retained for further evaluation of whether required information may be obtained and the status of the item converted to items new to system. Relevant information is entered for the item and a decision is made as to whether the item should be passed along for rating or flagged as pending for rating. Thereafter, the process described herein in additional detail is followed to the point of establishing star ratings for items identified suitable for inclusion in the star rating process.

The "Items new to system" selection makes available for viewing a listing of food items that have been stored in the Database 130 for the purpose of entering nutritional information used in rating the nutritional value for such items. Such food items may be manually or automatically entered into the Database 130, dependent upon the source of origin for the items. For example, a particular food retailer may have a master company database of all items it offers, including all food items. That master database may be arranged to "mark" all incoming food items as being of the type of retail item that should be entered into the Database 130 for subsequent rating through the rating algorithm. Alternatively, the new items that fall within the Items new to system category may come from other sources including, but not limited to, external suppliers.

The Items new to system are likely to enter the Database 130 without all pertinent nutritional information provided, without changed nutritional information provided, or with incomplete general item information. In other words, additional or corrective information may have to be inserted into the data set for that item. However, the initial item entry is from an external source, which source preferably provides the Universal Product Code (UPC) for each item. Therefore, in the form of the present invention described herein, the system 200 begins its functions after items have been provided. Relevant information regarding those provided items is then added or changed in the Database 130. However, it is to be understood that the system 200 can function to store item information where the item origin begins with the system 200.

An aspect of the present invention that addresses a particular omission in any prior databases of food information relates to prepared foods, referred to herein from time to time as recipes. The system 200 includes through functions 210-240 the option to include pertinent nutritional information about foods that may be prepared at the point of sale. Whereas prior food nutritional information reporting requirements were limited to manufactured foods sold in packaging with a Nutrition Facts panel, food items that are prepared on site, such as at a local delicatessen shop or food retailer, generally do not come with a Nutrition Facts panel. As a result, the consumer and, in this case, the system 200, would not be able to assess nutritional value for such recipes. The GUIs to be described herein enable the user to input pertinent nutritional information for such items by listing all ingredients in a recipe, gathering nutritional information for each ingredient and entering such information into the Database 130, and doing so for a specified serving size. The nutritional information for the individual ingredients of the recipe may come from one or more sources, including internal and external sources. As an example, a prepared sandwich comprising ham, cheese, lettuce, mayonnaise and bread can be evaluated for star rating using the system 200 by gathering the nutritional information for each component. The ham and lettuce information could come from a national source, such as the US Food and Drag Administration, while the cheese, mayonnaise and bread information may come from three separate manufacturers of those products. The present invention therefore enables a complete database of food nutritional information and scoring and rating for any type of food item, including recipes.

The "Items pending for rating" selection makes available for viewing information about all food items for which all required product information has been entered into the Database 130 for processing through the algorithm for star rating but that first require verification of the entered information prior to activating the rating algorithm for such item set. This includes newly included items as well as items for which nutritional or other information may have been changed and recalculation of nutritional value is required. The "Items rated" selection makes available for viewing information about all food items for which star ratings have been generated and made available for public viewing. The "Items flagged do not rate" selection makes available for viewing information about all food items for which there is not sufficient information available for processing through the algorithm for star rating, or for which there is no interest or need to process for a star rating. The "Items ready for rating" selection makes available for viewing information about all food items that are ready for star rating after all information for the item has been entered and verified. The number of food items in a particular selection is optionally indicated at 368.

Figure 5:
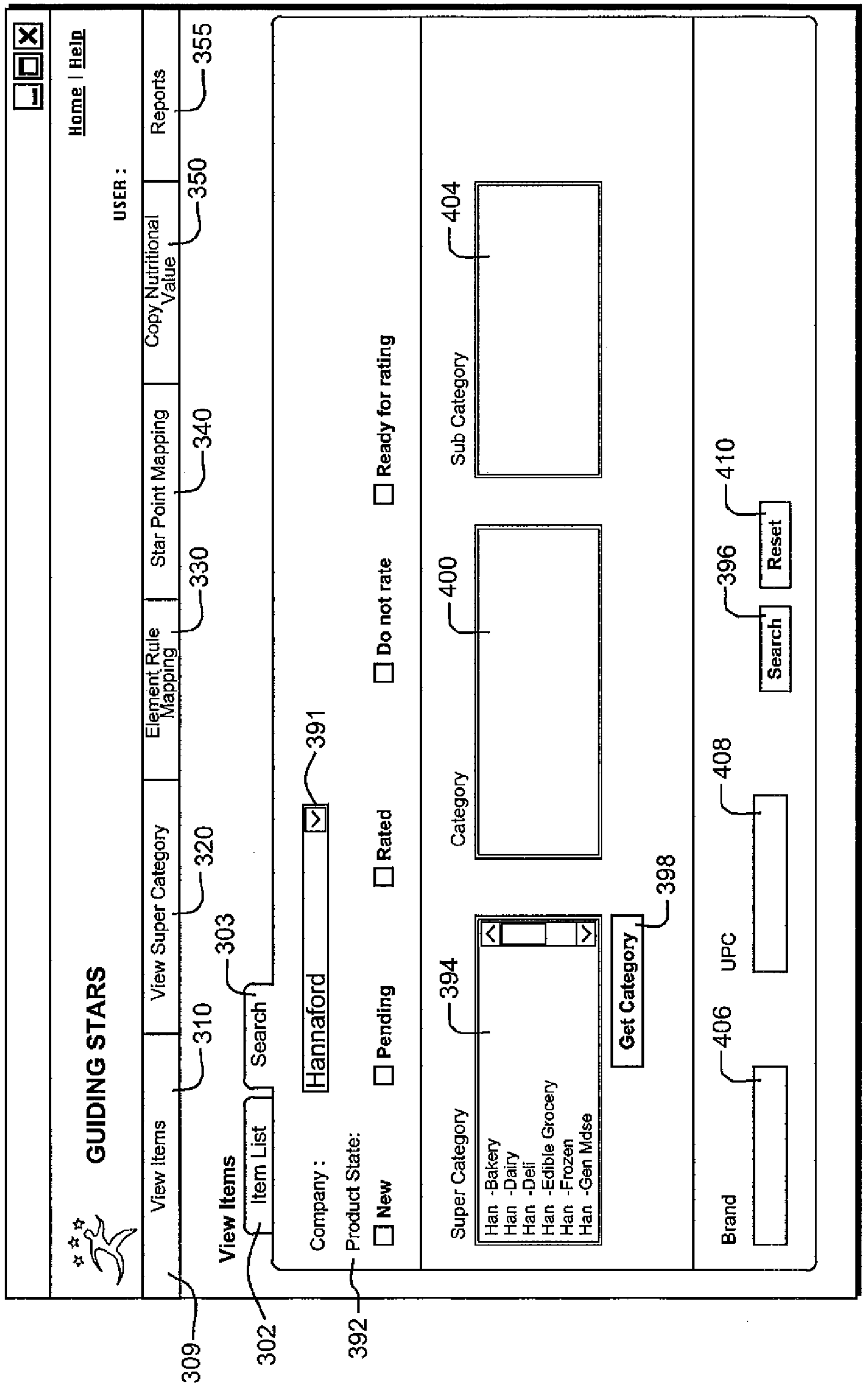
FIG. 5 is a display of a second screen representing an interface for a user to access the relational database by item searching through the primary section tab View Items.

When the user selects the Search tab 303 on the initial screen of FIG. 4, a GUI of the form represented in FIG. 5 is displayed. The GUI includes a primary functions tab set 309, including a View Items tab 310, a View Super Category tab 320, an Element Rule Mapping tab 330, a Star Point Mapping tab 340, a Copy Nutritional Value tab 350 and a Reports tab 355. The links provided through the primary functions tab set 309 enable the user to: 1) view, input and modify input details about the naming, content, and nutritional information of individual food items; 2) organize food information by primary categories; 3) view and modify food nutritional information valuing; 4) view and modify overall nutritional ratings based on valuing information; 5) copy information from one or more named food items to stored information associated with one or more other food items; and 6) generate reports of selectable form and format organized as desired by the user, with the reports providing any stored information of interest to the user.

The activation of the Search tab 303 produces a GUI that enables the user to select among a set of conditions for the purpose of returning from the Database 130 all food items meeting the set of conditions. The conditions include primary conditions of Company at 391 (a drop-down menu) and Product State at 392 (activation cells), corresponding to the primary conditions associated with the Item List tab 302. In particular, the "New" state corresponds to the "Items new to system" state, the "Pending" state corresponds to the "Items pending for rating" state, the "Rated" state corresponds to the "Items rated" state, the "Do not rate" state corresponds to the "Items flagged do not rate" state, and the "Ready for rating" state corresponds to the "Items ready for rating" state. The user can refine a food items listing by selecting one or more of the plurality of product state designations, whereas the Item List tab 302 allows selection of only one product state per search. Specifically, Search tab 303 allows the user to access item information based on Product State at 392 by enabling or disabling as search parameters any one or more of the indicated product state parameters. Additionally, the user may select a Super Category parameter from a set of the Super Categories displayed on first scroll menu 394 by highlighting one or more such parameters of interest. Search button 396 may then be activated to produce a set of all product items in that selected Super Category.

Additionally, the search may be refined by clicking Get Category button 398. Upon clicking the Get Category button 398 after selection of one or more Category parameters, a set of Categories is then displayed on second scroll menu 400. Search button 396 may then be activated to produce a set of all product items in the selected Category or Categories. The search may be still further refined by clicking a Get Sub Category button (not shown in FIG. 5 but similar to button 398). Upon clicking the Get Sub Category button after selection of a Category parameter, a set of Sub Categories is then displayed on third scroll menu 404. The user may select one or more Sub Category parameters from a set of the Sub Categories displayed on the third scroll menu 404 by highlighting such parameter(s) of interest. Search button 396 may then be activated to produce a set of all product items in the selected Sub Category(ies). The user may also select one or more items of interest from a listed supplier by entering supplier information in Brand frame 406, or a specific individual item by entering the unique product identifier in UPC frame 408 and then clicking on the Search button 396. The set of parameters selected to generate a search of the Database 130 for all items meeting the parameters may be cleared to establish new search parameters by clicking on Reset button 410. Clicking on the Search button 396 of FIG. 5 activates a screen display represented in FIG. 7.

In the example represented by the screen shown in FIG. 6, activated after the user has selected the Item List tab 302 of FIG. 4, the "Items new to system" product state has been selected and Show List tab 308 has been activated to produce a display of table 372. Table 372 is an example of an output generated by the computer program associated with the Database 130 of the present invention to present to a user information of interest regarding a particular selection of a set of food items. In table 372, column headings include UPC 374, Description 376, Super Category 378, Category 380, Sub Category 382, Setup Date 384 and Notes 385. The UPC 374 is the unique product identifier assigned by a manufacturer or other originator of a particular food type. The input information for the UPC 374 column is the SID_NBR entity identified in Tables 1-4. The Company Description 376 is the common language name or phrase for the particular food item as designated by the food item originator or modified by the Database 130 administrator or other authorized person. The input information for the Company Description 376 column is the CO_ID_CD entity identified in Tables 2, 9-11 and 14.

With continuing reference to table 372 of FIG. 6, the Super Category 378 is the common language alphanumeric name or phrase for the broadest grouping of food types within which the particular food item has been assigned. The input information for the Super Category 378 column is the SUPER_CATG_ID entity identified in Tables 2, 9, 11 and 14. The Category 380 is the common language alphanumeric name or phrase for the intermediate grouping of food types within which the particular food item has been assigned. The input information for the Category 380 column is the MJR_CATG_ID entity identified in Tables 2, 9, 11 and 14. The Sub Category 382 is the common language alphanumeric name or phrase for the most specific grouping of food types within which the particular food item has been assigned. The input information for the Sub Category 382 column is the INTMD_CATG_ID entity identified in Tables 2, 9, 11 and 14. The Setup Date 384 is the numeric timestamp of the date on which the particular food item was first entered into any master database used to supply the Database 130 or, alternatively, when the food item was first added to the Database 130. The input information for the Setup Date 384 column is the ADD_TS entity identified in Table 1. It is to be noted that the POST_DT entity identified in Table 1 may be employed to register most recent time when an item was designated "Ready for rating.". Finally, the Notes 385 column allows the user to access and add or view tracking notes associated with the item. For example, the tracking notes may be used to flag the indicated item for a check of missing information or a possible change of information, but is not limited thereto. The tracking notes may be entered manually or they may be imported from one or more sources. Further, the Notes 385 column may include a link to one or more photographs or other pieces of information about the item.

The example table 372 of FIG. 6 presents information for a set of ten food items. It is to be understood that the table 372 may be arranged to show more or fewer food items. A Next tab 386 may be activated to display the next set of food items for the selected category of food items. A Previous tab 388 may be activated to display a prior set of food items for the selected category of food items. Optionally, the information of a portion or all of the food items for a selected category may be transferred to another program application. For example, a link to a spreadsheet as one example of another program application, such as link 390, may be activated to enable the transfer of the selected information to the another program application.

The activation of the Search button 396 of FIG. 5 produces a GUI that enables the user to view all product items meeting the parameters established through the activation of the Search tab 303. The display is that of a results table 412 shown in FIG. 7, which includes the following column headings corresponding to the column headings of table 372 in FIG. 6: UPC 374, Description 376, Super Category 378, Category 380, Sub Category 382 and Notes 385. It also includes column heading Product State 414, a reference identifier for the rating status of each product item returned in the search. The "R" state indicates that the item has been rated. The input information for the Product State 414 column is the SRC_STAT_CD entity identified in Table 2.

The example table 412 of FIG. 7 presents information for a set of ten food items. It is to be understood that the table 412 may be arranged to show more or fewer food items. Next tab 386 may be activated to display the next set of food items for the selected category of food items. Previous tab 388 may be activated to display a prior set of food items for the selected category of food items. Optionally, the information of a portion or all of the food items for a selected category may be transferred to another program application. For example, a link to a spreadsheet as one example of another program application, such as link 390, may be activated to enable the transfer of the selected information to the another program application.

Activation of the Search 303 option that generates a product information table such as table 412 further permits the user to gain access to a set of report generation tools to be described herein, including a Product Score Card generated by clicking on Product Score Card Report link 416, Star Comparison Report 418 and Item Star Listing Report 420. Such reports may be generated for selectable sets of one or more product items by selecting the items through selection buttons located in column 422. Those selection buttons containing a check mark represent the product items for which a selected report is to be generated. These and other optional forms of reports to compare sets of items, items by specific originators (e.g., Company), and the like, may also be accessed by clicking on primary Reports tab 355.

Detailed information and screens for changing information about a specific item located in the Database 130 may be displayed by clicking on the UPC in UPC column 374 of either of tables 372 and 412. It is to be understood that different means for accessing an individual item may be created as desired. Clicking on the UPC of the particular item of interest activates a screen display such as the screen display of FIG. 8 depicting a particular selected item. Of course, the item of FIG. 8 is but one of many item examples available as a function of the number of items for which information is registered in the Database 130. The display of FIG. 8 permits a user to view and add or change a portion of information deemed to be relevant to the item selected. For example, first section 424 of the display includes information that cannot be modified or added regarding the item. On the other hand, second section 426 includes information that can be modified or added. The first section 424 includes UPC, Product Description, Super Category, Category, Sub Category, Star Rating, Recalculated Rating and Tracking Notes information.

With continuing reference to FIG. 8, the second section 426 includes windows for viewing, adding, changing or removing information associated with the selected item. It is to be understood that while FIGS. 8-12 for a representative individual food item show specific nutritional and other information incorporated therein, a newly added item would have no numbers inserted into the windows where such information is provided. Instead, a user would insert the information as gathered. Product serving size and servings per container input windows 428 permit the user to insert product size information provided by the supplier corresponding to product weight. The input information for the product serving size and servings per container input windows 428 are the PRDT_AMT and PRDT_UOM_CD entities identified in Table 1. The second section 426 also includes a brand input window 430, which permits the user to insert the brand of the product. The input information for the brand input window 430 is the BRND_NAM entity identified in Tables 1 and 9. Manufacturer input window 432 permits the user to insert the name of the original supplier of the food item. The input information for the manufacturer input window 432 is the MFR_NAM entity identified in Table 1. Further, the second section 426 includes a product description input window 434, which permits the user to insert a description of the product, which may be obtained from the product label. The input information for the product description input window 434 is the PRDT_LBL_DET_TXT entity identified in Table 1.

The second section 426 also includes a product warning input window 436, which permits the user to insert any warning information that may be located on the product label. The input information for the product warning input window 436 is the PRDT_LBL_WARN_TXT entity identified in Table 1. Ingredients input window 438 permits the user to insert any ingredient information provided by the product information supplier. That ingredient information is used in the calculation of food nutrition values. The input information for the ingredients input window 438 is the PRDT_LBL_INGR_TXT entity identified in Table 1. The information entered in the second section 426 for the particular item may be saved by activating save button 440. Alternatively, the information entered in the windows may be erased by activating the reset button 442, in which case any information existing prior to selecting the particular item will remain in the Database 130.

Scrolling down the window in which FIG. 8 is viewed, allows the user to display a screen showing detailed nutritional information for a selected item, an example of which is represented in FIG. 9. The nutritional information screen display of FIG. 9 depicts a set of four primary nutrition information tabs including Base Nutrients tab 444, a Vitamins tab 446, a Minerals tab 448 and an Other Nutrients tab 450. A Base Nutrients details view and input sheet 452 is displayed when the Base Nutrients tab 444 is activated. In an embodiment of the invention, the Base Nutrients input sheet 452 is the default initial nutrition information screen viewed when scrolling down from the screen shown in FIG. 8. The Base Nutrients sheet 452 includes windows for viewing, adding, changing or removing base nutrients information associated with the selected item. In the embodiment of the invention illustrated in FIG. 9, base nutrients are deemed to include calories, saturated fat, monounsaturated fat, cholesterol, sodium, potassium, dietary fiber and sugars. It is to be understood that the base nutrients may be selected to be a different set of components. The base nutrients information is obtained from the item information supplier including, for example, from a Nutrition Facts panel of a food item.

Product quantity input window set 454 permits the user to insert the amount of base nutrient identified for the item for each of the base nutrients. For example, in window 456, the quantity of the calories base nutrient has been entered as 40. The input information for the product quantity input window set 454 is the NUTRI_QTY entity identified in Table 4. Next, unit of measure input window set 458 permits the user to insert the unit of measure for the quantity of the base nutrient identified for the item for each of the base nutrients. For example, in window 460, the unit of measure for the calories base nutrient has been entered as kcal (kilocalories, which is the actual unit of measure but is often identified simply as calories). The input information for the unit of measure input window set 458 is the NUTRI_UOM_CD entity identified in Table 4. Finally, percent daily value input window set 462 permits the user to insert the percentage of recommended daily value of the particular base nutrient provided by the food item for each of the base nutrients. Other than for the calories category, the total recommended daily values for the identified base nutrients are established independently by the United States Food and Drug Administration and/or other applicable authorities. For example, in window 464, the percent daily value of the potassium base nutrient has been entered as 10. The input information for the windows of the percent daily value input window set 462 is the NUTRI_PCT entity identified in Table 4.

With continuing reference to FIG. 9, any information entered in any of the window sets may be saved by activating save button 466. Alternatively, the information entered in the windows may be erased by activating the reset button 468, in which case any information existing prior to entering changes in the windows will remain in the Database 130. The user further has the option to have the nutritional value and star ratings recalculated using the algorithm based on the introduction of new base nutrients information for the item by activating recalculate button 470. The user also has the option through the Base Nutrient sheet 452 to tag the item as one not to be calculated for nutritional value information by activating do not rate button 472. It is to be noted that the user may view a single display of all information for the selected item, including all nutrients information, item name, descriptions, categories and UPC, and nutritional value points and star rating by activating Product Score Card—Old link 474 to display all such information prior to saving and recalculating. After saving any information input changes using the save button 466 and initiating star rating recalculation using the recalculate button 470, the user may activate Product Score Card—New link 476 to view an update of the item information and nutritional value and star rating changes, if any, resulting from item information changes that were saved. Activation of link 474 generates a new screen of which an example is shown in FIGS. 13A and 13B. Activation of link 476 generates a new screen of which an example is shown in FIGS. 14A and 14B.

As shown in FIG. 10, a Vitamins details view and input sheet 478 is displayed when the Vitamins tab 446 is activated. The Vitamins sheet 478 includes a window for viewing, adding, changing or removing vitamins information associated with the selected item. In the embodiment of the invention illustrated in FIG. 10, vitamins are deemed to include Vitamin A, Vitamin C, Vitamin D, Vitamin A, Folate, Pantothenic Acid, Vitamin B12 and Vitamin B6. It is to be understood that the vitamins may be selected to be a different set of components. The vitamins information is obtained from the item information supplier including, for example, from a Nutrition Facts panel of a food item.

The Vitamins sheet 478 includes a single window set to permit the user to insert vitamin information. Percent daily value vitamin input window set 480 permits the user to insert the percentage of recommended daily value of the particular vitamin of the food item for each of the listed vitamins. The total recommended daily value is established independently by the United States Food and Drug Administration and/or other applicable authorities. For example, in window 482, the percent daily value of Vitamin A for the particular food item has been entered as 8. The input information for the input windows of the percent daily value vitamin input window set 480 is the NUTRI_PCT entity identified in Table 4.

With continuing reference to FIG. 10, any information entered in any of the windows may be saved by activating save button 466. Alternatively, the information entered in the windows may be erased by activating the reset button 468, in which case any information existing prior to entering changes in the windows will remain in the Database 130. The user further has the option to have the nutritional value and star ratings recalculated using the algorithm based on the introduction of new vitamins information for the item by activating recalculate button 470. The user also has the option through the Vitamins sheet 478 to tag the item as one not to be calculated for nutritional value information by activating do not rate button 472. It is to be noted that the user may view a single display of all information for the selected item, including all nutrients information, item name, descriptions, categories and UPC, and nutritional value points and star rating by activating Product Score Card—Old link 474 to display all such information prior to saving and recalculating as described with regard to FIG. 9. After saving any information input changes using the save button 466 and initiating star rating recalculation using the recalculate button 470, the user may activate Product Score Card—New link 476 to view an update of the item information and nutritional value and star rating changes, if any, resulting from item information changes that were saved as described with regard to FIG. 9.

As shown in FIG. 11, a Minerals details view and input sheet 484 is displayed when the Minerals tab 448 is activated. The Minerals sheet 484 includes a window for viewing, adding, changing or removing minerals information associated with the selected item. In the embodiment of the invention illustrated in FIG. 11, minerals are deemed to include Potassium, Calcium, Iron, Copper, Magnesium, Manganese, Molybdenum, Phosphorus, Selenium and Zinc. It is to be understood that the minerals may be selected to be a different set of components. The minerals information is obtained from the item information supplier including, for example, from a Nutrition Facts panel of a food item.

The Minerals sheet 484 includes a single window set to permit the user to insert mineral information. Percent daily value mineral input window set 486 permits the user to insert the percentage of recommended daily value of the particular mineral of the food item for each of the listed minerals. The total recommended daily value is established independently by the United States Food and Drug Administration and/or other applicable authorities. For example, in window 488, the percent daily value of Calcium for the particular food item has been entered as 4. The input information for the input windows of the percent daily value mineral input window set 484 is the NUTRI_PCT entity identified in Table 4.

With continuing reference to FIG. 11, any information entered in any of the windows may be saved by activating save button 466. Alternatively, the information entered in the windows may be erased by activating the reset button 468, in which case any information existing prior to entering changes in the windows will remain in the Database 130. The user further has the option to have the nutritional value and star ratings recalculated using the algorithm based on the introduction of new minerals information for the item by activating recalculate button 470. The user also has the option through the Minerals sheet 484 to tag the item as one not to be calculated for nutritional value information by activating do not rate button 472. It is to be noted that the user may view a single display of all information for the selected item, including all nutrients information, item name, descriptions, categories and UPC, and nutritional value points and star rating by activating Product Score Card—Old link 474 to display all such information prior to saving and recalculating as described with regard to FIG. 9. After saving any information input changes using the save button 466 and initiating star rating recalculation using the recalculate button 470, the user may activate Product Score Card—New link 476 to view an update of the item information and nutritional value and star rating changes, if any, resulting from item information changes that were saved as described with regard to FIG. 9.

As shown in FIG. 12, an Other Nutrients details view and input sheet 490 is displayed when the Other Nutrients tab 450 is activated. The Other Nutrients sheet 490 includes a window for viewing, adding, changing or removing information about any other nutrients considered to be relevant to the overall nutritional valuation associated with the selected item. In the embodiment of the invention illustrated in FIG. 12, other nutrients deemed to be of importance for inclusion in the calculation of a star rating include calories from fat, total fat, polyunsaturated fat, other carbohydrates, protein, Thiamin (Vitamin B11), Riboflavin (Vitamin B2), Niacin (Vitamin B3), Stearic Acid, carbohydrates and trans fatty acids. It is to be understood that the other nutrients may be selected to be a different set of components. The other nutrients information is obtained from the item information supplier including, for example, from a Nutrition Facts panel of a food item.

Other nutrients quantity input window set 492 permits the user to insert the amount of "other" nutrient identified for the item for each of the other designated nutrients. For example, in window 494, the quantity of the calories from fat nutrient has been entered as 0.0. The input information for the other nutrients quantity input window set 492 is the NUTRI_QTY entity identified in Table 4. Next, other nutrients unit of measure input window set 496 permits the user to insert the unit of measure for the quantity of the other nutrient identified for the item for each of the other nutrients. For example, in window 498, the unit of measure for the calories from fat nutrient has been entered as kcal. The input information for the other nutrients unit of measure input window set 496 is the NUTRI_UOM_CD entity identified in Table 4. Finally, other nutrients percent daily value input window set 500 permits the user to insert the percentage of recommended daily value of the particular other nutrient provided by the food item for each of the designated other nutrients. Other than for calories, the total recommended daily value is established independently by the United States Food and Drug Administration and/or other applicable authorities. For example, in window 502, the percent daily value of the number of grams of carbohydrates for the particular food item has been entered as 3. The input information for the windows of the other nutrients percent daily value input window set 500 is the NUTRI_PCT entity identified in Table 4.

With continuing reference to FIG. 12, any information entered in any of the windows may be saved by activating save button 466. Alternatively, the information entered in the windows may be erased by activating the reset button 468, in which case any information existing prior to entering changes in the windows will remain in the Database 130. As with the other product information nutrients GUIs, the user may view a single display of all information for the selected item, including all nutrients information, item name, descriptions, categories and UPC, and nutritional value points and star rating by activating Product Score Card—Old link 474 to display all such information as described with regard to FIG. 9. After saving any information input changes using the save button 466, the user may activate Product Score Card—New link 476 to view an update of the item information and nutritional value and star rating changes, if any, resulting from item information changes that were saved as described with regard to FIG. 9. Since the Other Nutrients details view and input sheet 490 is intended to be inclusive of all other nutrients considered to be of interest, Add Nutrient tab 504 is included as part of sheet 490 to enable the user to introduce additional nutrients of interest. Activating the Add Nutrient tab 504 produces for each activation an additional Nutrient Name input window generally at 506, with corresponding input windows for window sets 492, 496 and 500.

As illustrated in FIGS. 13 A and 13B, when the user activates the Product Score Card—Old link 474, a screen display is generated that depicts information about a food item for which a star rating has not been recalculated. As illustrated in FIGS. 14A and 14B, when the user activates the Product Score Card—New link 476, a screen display is generated that depicts information about a food item for which a star rating has been recalculated. That recalculation may have been performed after specific information about the item has been changed, after nutritional information valuing has been changed, the star rating algorithm has been modified, or any combination of the above. An advantage of the present invention is that the ability to recalculate nutritional values and ratings enables the user to conduct trial evaluations for food items. For example, if a particular food item has received a particular star rating and there is an interest in evaluating what types of changes may be required in the food item to improve its scoring, the user may make test adjustments to nutrient and/or ingredient information and then recalculate the item's rating. In that way, a food provider may be able to efficiently experiment with food ingredient changes by first assessing nutritional impact of contemplated changes using the system 200, and then making the changes to assess likeability, shelf life and any other attributes of interest. Alternatively, a contemplated food item may be set up in the system 200 as a "dummy" item and assesses for its prospective star rating. Verification and authorization features forming part of the system 200 minimize the possibility that a food item's star rating will be incorrectly presented to the public based on prospective ingredient changes rather than real ones. This feature of the present invention likely enhances the possibility that food suppliers will work to improve the nutritional qualities of their offerings.

FIGS. 13B and 14B are representations of screen displays of summarized nutritional information used in the value mapping of the food item, including element point mapping table 508 and Nutrition Facts Panel table 510. FIG. 13B represents the remainder of the information for the food item of FIG. 13A, although prior to any subsequent changes in item nutritional information. FIG. 14B represents the remainder of the information for the food item of FIG. 14A, after a change in item nutritional information. Element point mapping table 508 includes for the selected item an element name column 512, an element quantity column 514 and an element total points column 516. The element names of column 512 are those nutrient characteristics of the item that contribute to its point total, either as positive characteristics (positive numbers), or prospective negative characteristics that are excluded (negative numbers), wherein "nutrient density" is a generic term representing all of the vitamins and minerals identified in regard to FIGS. 10 and 11. The element quantities of column 514 are the quantity values of the indicated elements standardized to a 100 kcal (i.e., commonly referred to as calories) quantity so that all items of the Database 130 are standardized to a common quantity value for the purpose of making effective comparisons of nutritional value from one item to the next. The number at the bottom of column 514 is the star rating for that item based on its total element points. Finally, the total points attributed to all elements of the table 508 as established through the means described in the referenced pending application are tallied in column 516, with a total nutritional value number used to determine the star rating at cell 518.

The Nutrition Facts Panel table 510 depicts a manufacturer's serving size column 520, which includes the raw data of element quantities as provided by the item supplier in a serving size established by the supplier on the Nutrition Facts Panel of the item, if available. The table 510 further includes a standardized serving size column 522, which includes the corresponding element quantities as converted to the 100 kcal standardized serving quantity as generated by the system 200. It is to be noted that the displays represented in FIGS. 13A-14B provide the user with complete information about a specific item.

Upon returning to any one of the display screens such as the one represented in FIG. 5, the user may access a summary table of all items contained in the Database 130 based on designated Super Category by activating the View Super Category tab 320. As illustrated in FIG. 15, activation of the View Super Category tab 320 initiates an automated scan of the Database 130, compiling of the item information for each super category, and presentation in the form of Super Category table 600 of the summary total of all items contained in the Database 130. While the information may be represented in other ways, the example of Super Category table 600 includes a set of columns comprising a company name column 601, a super category column 602, items new to system column 604, items pending for rating column 606, items that cannot be rated column 608, items without nutritional information column 610, items with rating column 612, items flagged do not rate column 614, items ready for rating column 616 and total items column 618. The table 600 may be printed out by activating print button 620. The super categories established in an embodiment of the present invention include: bakery items, dairy items, deli items, edible grocery items, frozen items, general merchandise items, meat items, alternative items (Nature Place), produce items and seafood items. Other super category designations may be employed through modification of the Database 130.

By clicking on the Element Rule Mapping tab 330, the user may gain access to a display for viewing and/or modification of the values assigned to elements (nutritional components) of all food items of the Database 130. As illustrated in FIG. 16, the display generated by activating the Element Rule Mapping tab 330 includes a first element access section 630, a second element access section 632 and a third element access section 634. The first section 630 includes a high level search function wherein rating algorithm type drop down menu 636 may be accessed by clicking on drop down button 638 to allow selection of a rating algorithm based on food type. The first section 630 further includes a nutritional element drop down menu 640 that may be accessed by clicking on drop down menu 642 to allow selection of one of the nutritional element types used in the selected algorithm type such as, for example, any of the elements of table 508. Clicking on find button 644 generates the second section 632 and the third section 634. In the example shown in FIG. 16, the selected algorithm type was the general food types algorithm and the selected element type to view for nutritional valuing was saturated fat.

With reference to the example of accessing element valuing information for saturated fat associated with any food item assigned to the general foods type algorithm, the second section 632 of the display of FIG. 16 includes a nutrient keywords input window 646 and an ingredient keywords input window 648. The two windows 646 and 648 may be used to view, add or modify either or both of a rating element for that particular algorithm type, and/or to view, add or modify ingredient keywords to be flagged for determination whether a food item has such ingredient. The input to the Database 130 of the nutrient for the element rule mapping corresponds to the ELE_NAM entity of Table 6. By clicking on save button 650, the user may save the new or modified element name or ingredient designation to the Database 130, Alternatively, by clicking on reset button 652, the user cancels a contemplated adjustment and the screen display returns to the view of the second section 632 originally observed when first clicking on the find button 644.

The third section 634 also generated by clicking on the find button 644 includes a set of windows for viewing, adding, changing or removing element mapping information for designating nutritional values for each element represented in the element name drop down menu 640 of the first section 630. In the embodiment of the invention illustrated in FIG. 16, point input window set 654 permits the user to insert a series of point designations in integer form for the particular element saturated fat. The input information for the point input window set 654 is the ELE_PNT_VAL_QTY entity identified in Table 7. Next, range input window set 658 permits the user to select from a set of drop down menus comparators selected from <, >, ≤, ≥and =. For example, in window 660, the comparator has been entered as ≤. The input information for the range input window set 658 is the ELE_PNT_OPRTR_CD entity identified in Table 7.

Element value input window set 662 permits the user to insert a unit value of information for the selected element tied to the particular corresponding comparator of range input window set 658 that produces the point value of the similarly corresponding points of point input window set 654. The input information for the element value input window set 662 is the ELE_LMT_AMT entity identified in Table 7. Unit of measure input window set 666 permits the user to insert the unit of measure for the quantity of the nutrient selected. For example, in window 668, the unit of measure for the saturated fat nutrient has been entered as g (grams). The input information for the unit of measure input window set 666 is the ELE_UOM_CD entity identified in Table 7. The Is Present in Ingr input window set 669 allows the user to indicate whether the element type that may have a positive or negative impact on nutritional value rating by existence in the item rather than by specific quantity does or does not exist in the item. By clicking on save button 670, the user may save the new or modified element rule mapping values and limits for use in the star rating algorithm. Alternatively, by clicking on reset button 672, the user cancels a contemplated adjustment of the assigned values and limits and the screen display returns to the view of the third section 634 originally observed when first clicking on the find button 644.

When the rules for valuing a particular nutritional element, such as saturated fat or cholesterol, for example, has been modified, the system of the present invention generates a confirmation GUI when the save button 670 of the third section 634 of FIG. 16 has been activated. This generation is preferably automated, although not limited thereto, as a safety feature to ensure that the system administrator has determined rule changes are justified and to check that the rule changes have been modified as desired. More generally, it is to be noted that any or all of the input GUIs may have restricted access rights to ensure Database 130 and algorithm integrity. Such security may be achieved through appropriate authentication and access rules established in the course of the development of the Database 130 and the related access programs.

In the embodiment of the present invention described herein, when the save button 670 of FIG. 16 has been activated, a display screen such as represented in FIG. 17 is generated in regard to changes to be made for a specific element modified in FIG. 16. The screen of FIG. 17 depicts an existing rules section 674 and a modified rules section 676. This split arrangement allows the user to readily view both the original element rule information of section 674 and any changes made to that information as shown in section 676. If any unacceptable changes have been made, cancel button 678 is activated and the display returns to the screen of the form represented in FIG. 16. On the other hand, if the modified information of section 676 is considered acceptable, save button 680 is activated to finally save to the Database 130 and the related algorithm the element rule changes made in the screen of FIG. 16.

By clicking on the Star Point Mapping tab 340 from any prior screen including the primary tabs set, the user may gain access to a star mapping window 682 for viewing and/or modification of the star ratings assigned to the element value totals for all food items of the Database 130. That is, for each food item for which nutritional information has been generated and the element valuing has been established, a star rating may be calculated using the algorithm based on star mapping to value totals. As illustrated in FIG. 18, the display generated by activating the Star Point Mapping tab 340 includes a set of windows for viewing, adding, changing or removing star point mapping information for designating star ratings for element point totals for particular primary food groupings. In the embodiment of the invention illustrated in FIG. 18, there are three primary food groupings shown, General, Meat and Baby food. However, it is to be understood that additional food groupings may be added as desired. The availability of a plurality of food groupings allows the administrator to adjust star rating calculations without changing entire element valuing rules for specific nutritional elements.

The display of FIG. 18 includes a star designation column 684 with representative illustrations of star ratings comprising three stars, two stars, one star and no stars. The star designations are described more fully in the referenced co-pending application. A first input window set of FIG. 18 is a range input window set 686, which permits the user to select from a set of drop down menus comparators selected from $<$ and $\geq$. For example, in window 688, the comparator for the two stars designation has been entered as $\geq$. The input information for the range input window set 686 is the ELE_PNT_VAL_QTY entity identified in Table 7 accompanying this disclosure. A second input window set is a first points input windows set 690, which permits the user to insert an integer point value tied to the particular corresponding comparator of range input window set 686 that produces the star value of the similarly corresponding star designations of star designation column 684 for a first food grouping valued based on a rating algorithm established for that group. The input information for the first points input windows set 690 is the PRDT_RATG_CD entity identified in Table 1.

A third input window set is a second points input windows set 694, which permits the user to insert an integer point value tied to the particular corresponding comparator of range input window set 686 that produces the star value of the similarly corresponding star designations of star designation column 684 for a second food grouping valued based on a rating algorithm established for that group. The input information for the second points input windows set 694 is the PRDT_RATG_CD entity identified in Table 1. A fourth input window set is a third points input windows set 696, which permits the user to insert an integer point value tied to the particular corresponding comparator of range input window set 686 that produces the star value of the similarly corresponding star designations of star designation column 684 for a third food grouping valued based on a rating algorithm established for that group. The input information for the third points input windows set 696 is the PRDT_RATG_CD entity identified in Table 1. By clicking on save button 698, the user may save any modifications made to the star point mapping values and limits for use in the star rating algorithm. Alternatively, by clicking on reset button 700, the user cancels a contemplated adjustment of the assigned values and limits and the screen display of FIG. 18 returns to its original values and limits.

FIG. 19 illustrates the screen display that is generated when the Copy Nutritional Value tab 350 is activated. That screen includes an arrangement to enable the user to copy all inputted information of one or more food items of the Database 130 into the corresponding information set for a second set of one or more food items, either newly added to the Database 130 or for which existing information is to be modified. From Company window set 701 includes drop down menus from which the user may select one company name to establish an initial set of items from which copying selections may be made. From UPC window set 702 includes windows into which the user inserts the specific UPC designations of one or more items having information to be transferred. To Company window set 703 includes drop down menus from which the user may select one company name to identify to which company subset the selected items are to be transferred. To UPC window set 704 includes windows into which the user inserts the specific UPC designations of one or more items into which the information from the UPCs of window set 702 is to be received. Upon completing the windows as desired, the copying of information from the individual items represented in the From UPC window set 702 to the To UPC window set 704, may be activated for changing the Database 130 by clicking on Add button 708 and submit button 710. If that change is not desired, reset button 712 may be activated to remove all UPC designations of both window sets.

FIG. 20 illustrates the screen display that is generated when the Reports tab 350 is activated. That screen includes a report selection window 714 with two options for the type of report to be provided regarding star ratings determined. A super category report may be generated by check marking box 716 for the Star wise Super Category Report. A super category report enables the user to observe the star ratings for a broad set of food items. A category report may be generated by check marking box 718 for the Star wise Category Report. A category report enables the user to observe the star ratings for a subset of a particular food type within the broader super category grouping. The user may further select by Company name the information provided in a generated report. Specifically, by highlighting one or more company names from first drop down menu 720, the user may refine the Star wise Super Category Report to focus on the relevant super category information for a particular, supplier, manufacturer, retailer or the like. Alternatively, by highlighting one or more company names from second drop down menu 722, the user may refine the Star wise Category Report to focus on the relevant category information for a particular, supplier, manufacturer, retailer or the like. Upon completing the category and company name selections as desired, the generation of the report may be activated by clicking on Submit button 724.

While the particular content of the reports available through the window of FIG. 20, the system 200 of the present invention enables a user to generate reports comprising many types of selectable parameters. Such selections may be made directly through the system 200 or by exporting data from a selected set and generating a separate report, such as through a spreadsheet application, for example. The food item data stored in the Database 130 may be accessed to generate such selectable reports based on Company (e.g., vendor) name, by particular nutrient components, by particular ingredients—including any potential allergens, by nutrient or ingredient limits, by caloric values, by serving sizes, by element point values, by individual element limits, or any other set of parameters of interest to the user. In other words, the arrangement of the Database 130 allows the user to filter for any information set of interest. This ability to "slice and dice" the data as desired through the design and structure of the Database 130 and the system 200, allows the user to gather and review broad sets of information as well as very specific sets of information and anything in between. This function of the present invention is a substantial improvement over any food product information database previously available for use as it enables the user to focus in on particular food information, review it, value it, rate it and, as a result, to conveniently make assessments about individual food items and sets of food items. This data filtering capability for a very large food product set is of value to food retailers, food manufacturers, food developers and nutrition researchers.

Having thus described at least one illustrative embodiment of the invention, various alterations, modifications and improvements are contemplated by the invention. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. A non-transitory computer-readable medium encoded with a data structure operable in a computer system with one or more computer-implemented functions, the data structure comprising:

one or more food product information tables including entities for: identifying one or more food products, each by a unique identifier, listing ingredients of each food product, and listing nutritional information of each food product;

a nutritional element mapping table including an element name field for selecting a nutritional element associated with a food product to be rated based on information of the one or more food product information tables, a nutrient keywords field for inputting one or more nutritional element keywords, an element rules point field for inputting one or more nutritional element point values associated with the selected nutritional element and an element rules range field for inputting one or more ranges of nutritional element input values associated with the selected nutritional element;

a rating mapping table for designating a rating algorithm type for one or more of the one or more food products, wherein the rating mapping table is configured to permit selection of a particular rating algorithm type based on food type selection, wherein a value or values of either or both of the element rules point field and the element rules range field of the nutritional element mapping table may be modified based on the rating algorithm type designated; and a point mapping table for generating a nutritional rating for each of the one or more food products determined using the particular rating algorithm designated as a function of the food type selection for each of the one or more food products, wherein each of the rating algorithm types is configured to calculate a total point value based on the element rules point field and the element rules range field used for the food type selection and generating the nutritional rating based on the total point value calculated.

2. The non-transitory computer-readable medium of claim 1 wherein the data structure further includes a product label table, wherein the product label table includes entities for food product super category and category.

3. The non-transitory computer-readable medium of claim 1 wherein the data structure further includes a recipe table.

4. The non-transitory computer-readable medium of claim 1 wherein the data structure further includes a nutrition master table.

5. The non-transitory computer-readable medium of claim 1 wherein the entities of the one or more food product information tables include either or both of local unique products information and remote unique products information.

6. The non-transitory computer-readable medium of claim 1 wherein the data structure further includes an exceptions table.

7. The non-transitory computer-readable medium of claim 1 wherein one or more of the entities of the one or more food product information tables are designated as Primary Key entities and a remainder of the entities are designated as Foreign Key entities, wherein the Primary Key entities have one and only one value throughout all of the one or more food product information tables and wherein the Foreign Key entities link entities, tables or entities and tables together.

8. The non-transitory computer-readable medium of claim 1 wherein the data structure is configured to enable a user to selectably display nutritional information and rating information for one or more of the one or more food products based on nutritional rating.

9. The non-transitory computer-readable medium of claim 1 wherein the data structure is configured to enable a user to selectably display nutritional information and rating information for one or more of the one or more food products based on company name.

10. The non-transitory computer-readable medium of claim 1 wherein ingredient and nutritional information for each product comes from one or both of an external source and an internal source.

11. The non-transitory computer-readable medium of claim 1 wherein the data structure is configured to group the one or more food items based on product state selected from the group consisting of items new to system, items pending for rating, items rated, items flagged do not rate and items ready for rating.

12. The non-transitory computer-readable medium of claim 1 wherein the data structure is configured to enable the user to modify food product ingredient or nutritional information and recalculate the nutritional rating.

13. The non-transitory computer-readable medium of claim 1 wherein the data structure is configured to enable the user to combine nutritional information obtained for a plurality of components of a prepared food product into a single combined nutritional information set suitable for calculating the nutritional rating of the prepared food product.

14. The non-transitory computer-readable medium of claim 1 wherein the data structure is configured to enable the user to set up a dummy food product type, calculate nutritional rating for the dummy food product, modify nutritional information for the dummy food product, and recalculate the nutritional rating.

15. The non-transitory computer-readable medium of claim 1 wherein the data structure is configured to enable a user to select one or more portions of information and report such selected portions in a format of interest.

16. A memory for storing data for access by an application program being executed on a computer processing system, comprising:

a data structure stored in the memory, the data structure including information resident in a database used by the application program, the database including:

one or more food product information tables including entities for: identifying one or more food products, each by a unique identifier, listing ingredients of each food product, and listing nutritional information of each food product;

a nutritional element mapping table including an element name field for selecting a nutritional element associated with a food product to be rated based on information of the one or more food product information tables, a nutrient keywords field for inputting one or more nutritional element keywords, an element rules point field for inputting one, or more nutritional element point values associated with the selected nutritional element and an element rules range field for inputting one or more ranges of nutritional element input values associated with the selected nutritional element;

a rating mapping table for designating a rating algorithm type for one or more of the one or more food products, wherein the rating mapping table is configured to permit selection of a particular rating algorithm type based on food type selection, wherein a value or values of either or both of the element rules point field and the element rules range field of the nutritional element mapping table may be modified based on the rating algorithm type designated; and a point mapping table for generating a nutritional rating for each of the one or more food products determined using the particular rating algorithm designated as a function of the food type selection for each of the one or more food products, wherein each of the rating algorithm types is configured to calculate a total point value based on the element rules point field and the element rules range field used for the food type selection and generating the nutritional rating based on the total point value calculated.

17. The memory of claim 16 further comprising a product label table, wherein the product label table includes entities for food product super category and category.

18. The memory of claim 16 further comprising a recipe table.

19. The memory of claim 16 further comprising a nutrition master table.

20. The memory of claim 16 further comprising an elements point table.

21. The memory of claim 20 further comprising a sub elements table.

22. The memory of claim 16 further comprising an exceptions table.

23. The memory of claim 16 wherein one or more entities of the one or more food product information tables are designated as Primary Key entities and a remainder of the entities are designated as Foreign Key entities, wherein the Primary Key entities have one and only one value throughout all of the one or more food product information tables and wherein the Foreign Key entities link entities, tables or entities and tables together.

24. A non-transitory computer-readable medium with computer executable instructions that direct a computing system to operate a database, the database comprising:

one or more food product information tables including entities for: identifying one or more food products, each by a unique identifier, listing ingredients of the one or more food products, and listing nutritional information of each food product;

a nutritional value mapping function including an element name field for selecting a nutritional element associated with a food product to be rated based on information of the one or more food product information tables, a nutrient keywords field for inputting one or more nutritional element keywords, an element rules point field for inputting one or more nutritional element point values associated with the selected nutritional element and an element rules range field for inputting one or more ranges of nutritional element input values associated with the selected nutritional element, wherein the computer-readable medium further includes a rating function executable by the computing system for designating a rating algorithm type for each food product, wherein the rating function is configured to: a) permit selection of a particular rating algorithm type based on food type selection, wherein a value or values of either or both of the element rules point field and the element rules range field may be modified based on the rating algorithm type designated; b) generate a nutritional rating for each of the one or more food products determined using the particular rating algorithm designated as a function of the food type selection for each of the one or more food products, wherein each of the rating algorithm types is configured to calculate a total point value based on the element rules point field and the element rules range field used for the food type selection and generating the nutritional rating based on the total point value calculated; and to enable a user to selectably display nutritional information and nutritional rating information for one or more of the one or more food products based on company name.

25. The non-transitory medium of claim 24 with computer-executable instructions to enable the user to group the one or more food items based on product state selected from the group consisting of items new to system, items pending for rating, items rated, items flagged do not rate and items ready for rating.

26. The non-transitory medium of claim 24 with computer-executable instructions to enable the user to modify food product ingredient or nutritional information and recalculate the star rating.

27. The non-transitory medium of claim 24 with computer-executable instructions to enable the user to set up a dummy food product type, calculate a star rating for the dummy food product, modify nutritional information for the dummy food product, and recalculate the star rating.

28. A method implemented, at least in part, by a computing system configured to carry out executable instructions using computer-implemented functions, the method comprising the steps of:

a. maintaining one or more food product information tables;

b. identifying in the one or more tables one or more food products, each by a unique identifier;

c. listing ingredients of the one or more food products;

d. listing nutritional information of the one or more food products;

e. identifying nutritional value element mapping based on food product nutritional information, nutritional elements, nutritional element point values associated with the nutritional elements and one or more ranges of nutritional element input values associated with the nutritional elements;

f. designating a rating algorithm type for each food product type using a nutritional rating function, wherein the nutritional rating function is configured to permit selection of a particular rating algorithm type based on food type selection; and g. generating a nutritional rating for each of the one or more food products determined using the particular rating algorithm designated as a function of the food type selection for each of the one or more food products, wherein each of the rating algorithm types is configured to calculate a total point value based on the element point values and the one or more ranges used for the food type selection and generating the nutritional rating based on the total point value calculated.

29. The method of claim 28 further comprising the step of generating one or more reports displaying nutritional information for one or more of the one or more food products based on selectable nutritional information.

30. The method of claim 28 further comprising the step of generating one or more reports displaying nutritional information and rating information for one or more of the one or more food products based on selectable nutritional rating.

31. The method of claim 28 further comprising the step of generating one or more reports displaying nutritional information and rating information for one or more of the one or more food products based on company name.

32. The method of claim 28 further comprising the step of grouping the one or more food items based on product state selected from the group consisting of items new to system, items pending for rating, items rated, items flagged do not rate and items ready for rating.

33. The method of claim 28 further comprising the steps of:

a. modifying food product ingredient or nutritional information; and b. recalculating nutritional rating.

34. The method of claim 28 further comprising the steps of a. setting up a dummy food product in the one or more food product information tables;

b. calculating a nutritional rating for the dummy food product;

c. modifying the nutritional information for the dummy food product; and d. recalculating the nutritional rating for the dummy food product.

* * * * *

UNITED STATES PATENT AND TRADEMARK OFFICE

CERTIFICATE OF CORRECTION

PATENT NO. : 8,626,796 B2
APPLICATION NO. : 11/848663
DATED : January 7, 2014
INVENTOR(S) : James L. McBride et al.

It is certified that error appears in the above-identified patent and that said Letters Patent is hereby corrected as shown below:

In the Specification

Figure 3A:
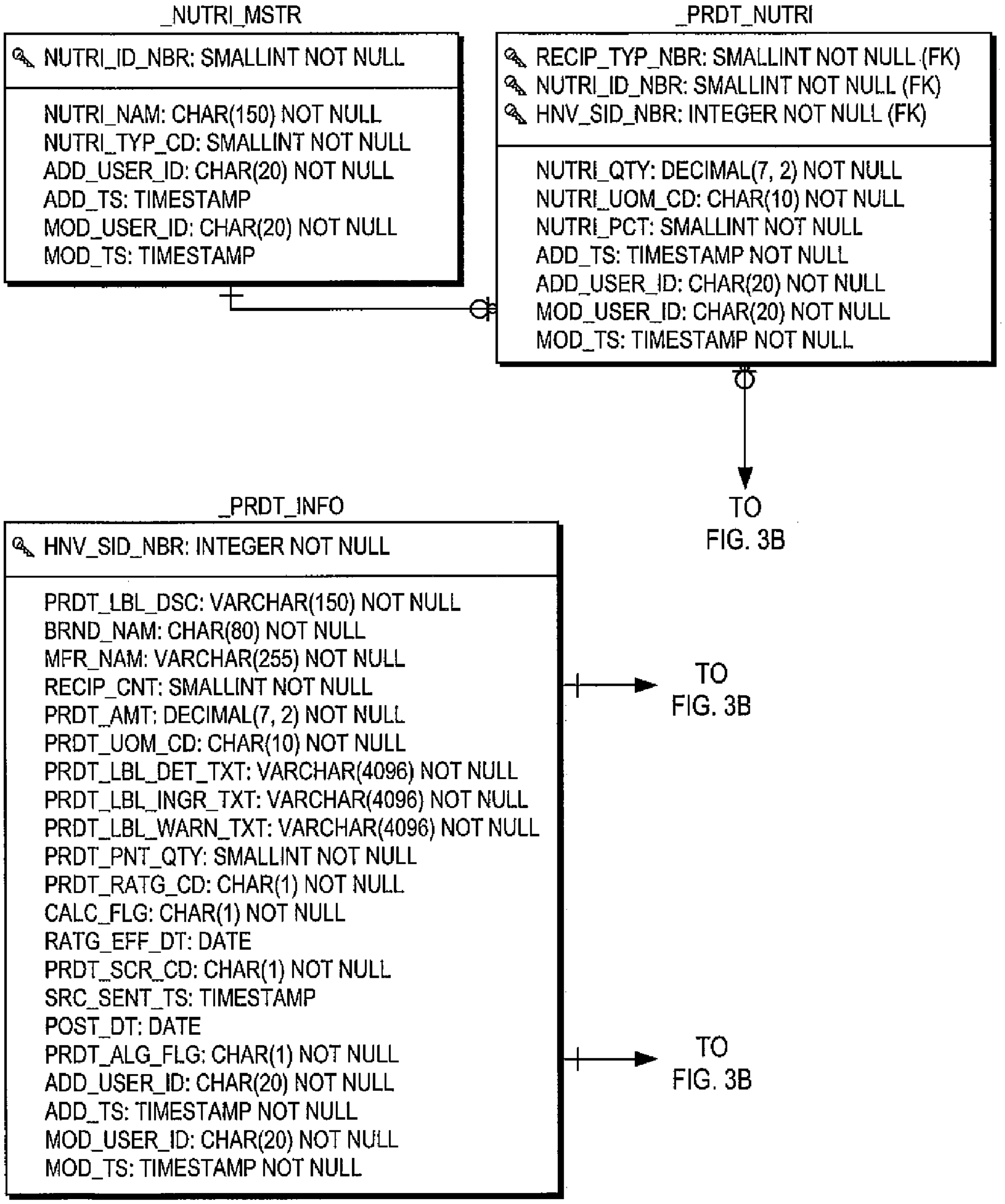
FIG. 3A is a first portion of a simplified representation of the relational database of the present invention.
Figure 3B:
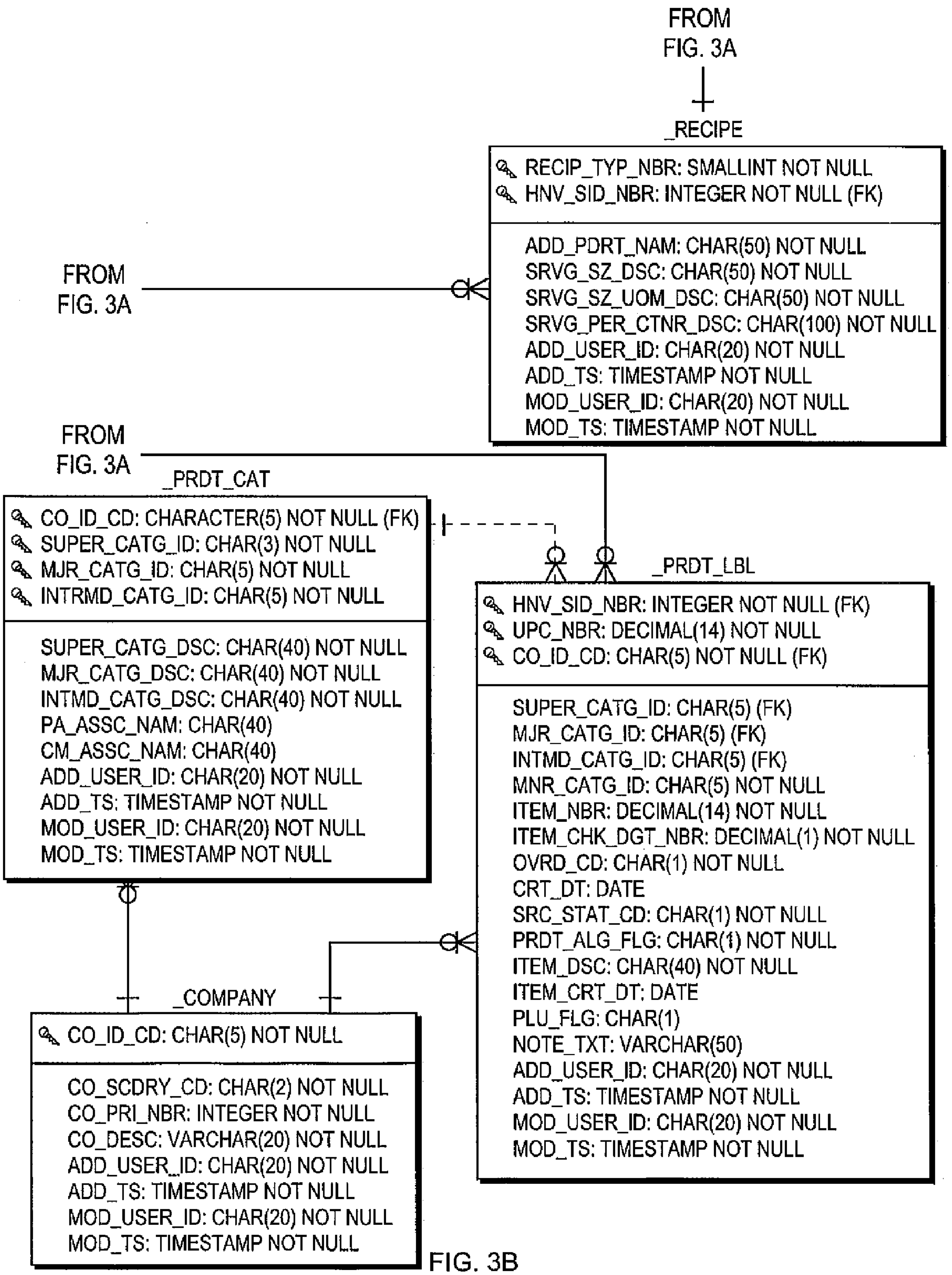
FIG. 3B is a second portion of a simplified representation of the relational database of the present invention.
Figure 3C:
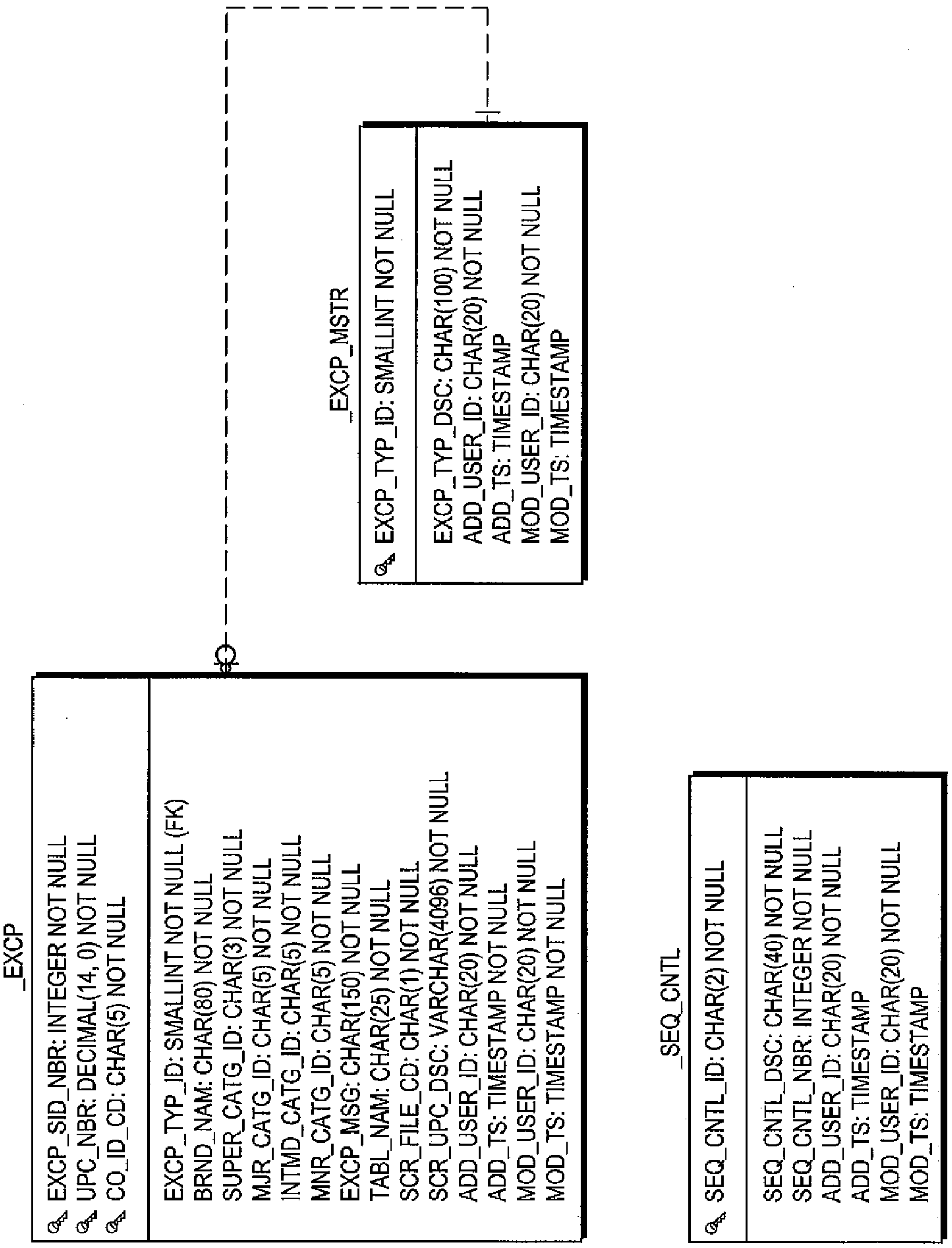
FIG. 3C is a third portion of a simplified representation of the relational database of the present invention.
Figure 3D:
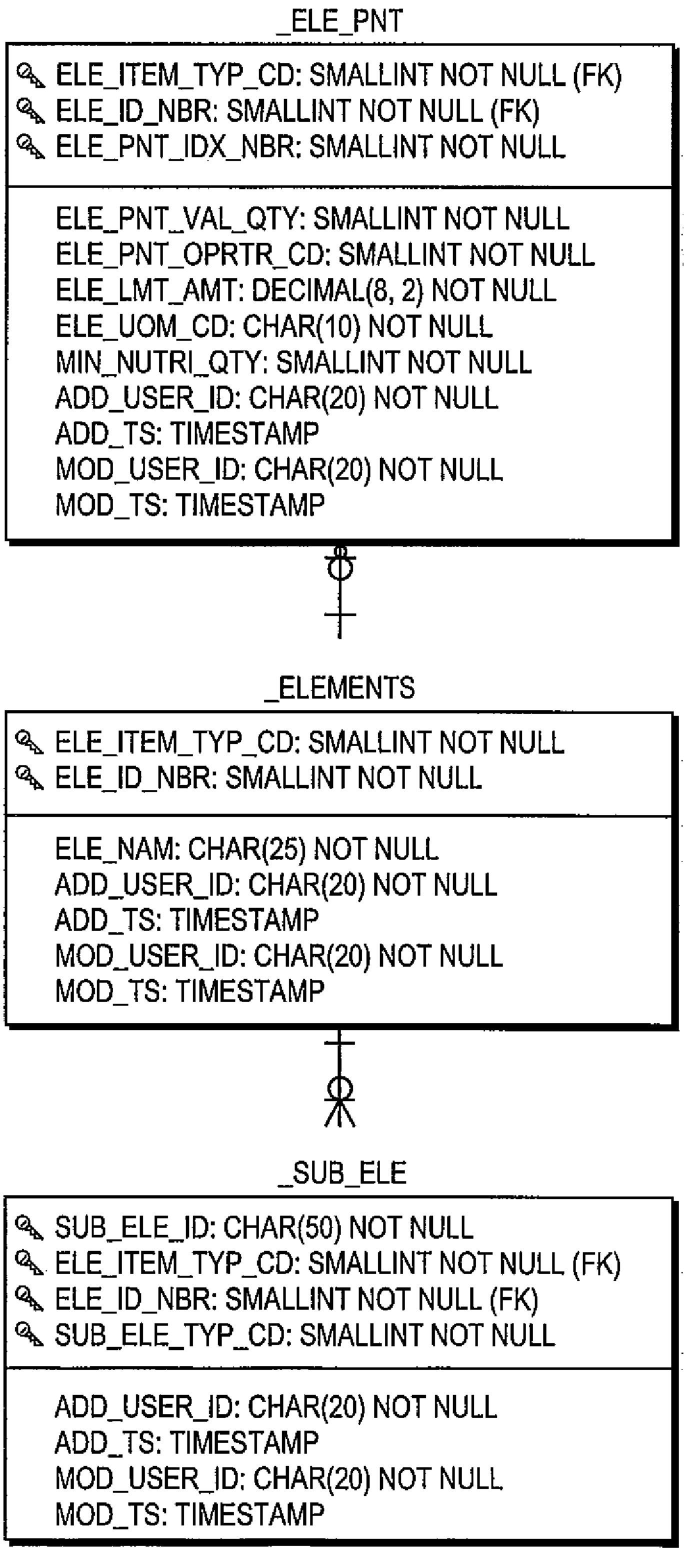
FIG. 3D is a fourth portion of a simplified representation of the relational database of the present invention.

Column 4, lines 42-44, "FIG. 3D is a fourth portion of a simplified representation of of the relational database invention." should be deleted.

Column 7, line 4, "(USA)" should be changed to --(ISA)--.

Column 14, line 5, "CO_ID--CD" should be changed to --CO_ID_CD--.

Column 24, line 18, "Drag" should be changed to --Drug--.

Column 29, line 29, "Vitamin A" should be changed to --Vitamin E--.

In the Claims

Column 38, line 66, "one," should be changed to --one--.

Signed and Sealed this
Twentieth Day of May, 2014

Michelle K. Lee

Michelle K. Lee
*Deputy Director of the United States Patent and Trademark Office*